(12) United States Patent
Gopalan et al.

(10) Patent No.: US 7,563,900 B2
(45) Date of Patent: Jul. 21, 2009

(54) PROCESS FOR THE PREPARATION N-(3,5-DICHLOROPYRID-4-YL)-4-DIFLUOROMETHOXY-8-METHANE SULFONAMIDO-DIBENZO[B,D]FURAN-1-CARBOXAMIDE

(75) Inventors: Balasubramanian Gopalan, Mumbai (IN); Laxmikant A. Gharat, Maharashtra (IN); Batchu Chandrasekhar, Hosur (IN); Bijukumar G. Pillai, Navi Mumbai (IN)

(73) Assignee: Glenmark Pharmaceuticals S.A., La Chaux-de-Fonds (CH)

( * ) Notice: Subject to any disclaimer, the term of this patent is extended or adjusted under 35 U.S.C. 154(b) by 515 days.

(21) Appl. No.: 11/251,567

(22) Filed: Oct. 13, 2005

(65) Prior Publication Data

US 2006/0135779 A1    Jun. 22, 2006

Related U.S. Application Data

(60) Provisional application No. 60/621,981, filed on Oct. 21, 2004, provisional application No. 60/618,474, filed on Oct. 13, 2004.

(30) Foreign Application Priority Data

Oct. 14, 2004    (IN) .................. 1099/MUM/2004

(51) Int. Cl.
    C07D 307/91    (2006.01)
    C07D 405/06    (2006.01)
    C07C 205/06    (2006.01)

(52) U.S. Cl. .................... 546/284.1; 549/460; 549/461; 568/424

(58) Field of Classification Search .............. 549/460, 549/461; 568/424
See application file for complete search history.

(56) References Cited

U.S. PATENT DOCUMENTS

| | | | |
|---|---|---|---|
| 3,759,948 A | 9/1973 | Shen et al. | |
| 4,222,944 A | 9/1980 | Berger et al. | |
| 5,814,651 A | 9/1998 | Duplantier et al. | |
| 6,514,996 B2 | 2/2003 | Ohshimaet et al. | |
| 7,223,789 B2 * | 5/2007 | Gopalan et al. | 514/437 |

FOREIGN PATENT DOCUMENTS

| | | |
|---|---|---|
| DE | 2059358 | 6/1971 |
| EP | 62158253 | 7/1987 |
| EP | 0 497 564 A1 | 8/1992 |
| EP | 1 270 577 A1 | 1/2003 |
| GB | 1041861 | 2/1963 |
| GB | 1285398 | 8/1972 |
| WO | WO 92/10476 A1 | 6/1992 |
| WO | WO 93/19747 A1 | 10/1993 |
| WO | WO 94/02465 A1 | 2/1994 |
| WO | WO 94/08995 A1 | 4/1994 |
| WO | WO 94/20446 A1 | 9/1994 |
| WO | WO 95/01338 A1 | 1/1995 |
| WO | WO 95/04046 A1 | 2/1995 |
| WO | WO 95/09837 A1 | 4/1995 |
| WO | WO 95/20578 A1 | 8/1995 |
| WO | WO 95/24381 A1 | 9/1995 |
| WO | WO 98/09934 A1 | 3/1998 |
| WO | WO 99/47545 A2 | 9/1999 |
| WO | WO 01/27107 A2 | 4/2001 |
| WO | WO 01/70673 A2 | 9/2001 |
| WO | WO 01/70746 A1 | 9/2001 |
| WO | WO 02/060867 A2 | 8/2002 |
| WO | WO 02/072567 A2 | 9/2002 |
| WO | WO 2004/016596 A1 | 2/2004 |
| WO | WO 2004/022536 A1 | 3/2004 |
| WO | WO 2004/037805 A1 | 5/2004 |
| WO | WO-2004/089940 | 10/2004 |

OTHER PUBLICATIONS

Koyama et al., Heterocycles 1981; 16(6):969-972.
Hulme et al., Bioorganic and Medicinal Chemistry Letters 1998; 8:175-178.
Silvestre et al., Drugs of the Future 1998; 23(6):607-615.
Fox et al., J. Med. Chem. 2002; 45(2):360-370.

* cited by examiner

Primary Examiner—Bernard Dentz
(74) Attorney, Agent, or Firm—Darby & Darby P.C.

(57) ABSTRACT

The present invention relates to a method of preparing N-(3,5-dichloropyrid-4-yl)-4-difluoromethoxy-8-methane-sulfonamido-dibenzo[b,d]furan-1-carboxamide and pharmaceutically acceptable salts thereof, such as its sodium salt, and novel intermediate compounds useful in the synthesis of the aforementioned compound.

33 Claims, No Drawings

PROCESS FOR THE PREPARATION N-(3,5-DICHLOROPYRID-4-YL)-4-DIFLUOROMETHOXY-8-METHANE SULFONAMIDO-DIBENZO[B,D]FURAN-1-CARBOXAMIDE

This application claims the benefit of U.S. Provisional Application No. 60/618,474, filed Oct. 13, 2004, Indian Provisional Application No. 1099/Mum/2004, filed Oct. 14, 2004, and U.S. Provisional Application No. 60/621,981, filed Oct. 21, 2004, both of which are hereby incorporated by reference.

FIELD OF THE INVENTION

The present invention relates to a method of preparing N-(3,5-dichloropyrid-4-yl)-4-difluoromethoxy-8-methanesulfonamido-dibenzo[b,d]furan-1-carboxamide and pharmaceutically acceptable salts thereof, such as its sodium salt, and novel intermediate compounds useful in the synthesis of the aforementioned compound.

BACKGROUND OF THE INVENTION

Although several research groups all over the world are working to find highly selective PDE-4 isozyme inhibitors, so far success has been limited. Various compounds have shown PDE-4 inhibition. SmithKline Beecham's "Ariflo", Byk Gulden's Roflumilast and Bayer's Bay-19-8004 have reached advanced stage of human clinical trials. Other compounds which have shown potent PDE-4 inhibitory activity include Celltech's CDP-840, Schering Plough's D-4418, Pfizer's 5CP-220,629, Parke Davis's PD-168787 and Wyeth's Filaminast. However, recently due to efficacy and side effects problems, Ariflo, CDP-840 and Bay-19-8004 were discontinued from clinical trials as a treatment for asthma. D-4418 and 5CP-220,629 are presently undergoing phase-1 clinical trials.

International Publication No. WO 2004/089940 discloses heterocyclic PDE-4 inhibitors, N-(3,5-dichloropyrid-4-yl)-4-difluoromethoxy-8-methanesulfonamido-dibenzo-[b,d]furan-1-carboxamide and pharmaceutically acceptable salts thereof, useful in the treatment of certain allergic and inflammatory diseases, such as asthma and chronic obstructive pulmonary disease (COPD).

There remains a need for alternative methods for preparing N-(3,5-dichloropyrid-4-yl)-4-difluoromethoxy-8-methanesulfonamido-dibenzo[b,d]furan-1-carboxamide and pharmaceutically acceptable salts thereof.

BRIEF SUMMARY OF THE INVENTION

The present invention provides new methods for the preparation of N-(3,5-dichloropyrid-4-yl)-4-difluoromethoxy-8-methanesulfonamido-dibenzo[b,d]furan-1-carboxamide or a pharmaceutically acceptable salt thereof, such as its sodium salt.

One aspect of the invention is a method for the preparation of 4-cyclopentyloxy-3-(4'-nitro-2'-bromo phenoxy)-benzaldehyde (C) by reacting 4-cyclopentyloxy-3-hydroxy-benzaldehyde (B) with 3-bromo-4-fluoro nitrobenzene ($B^1$)

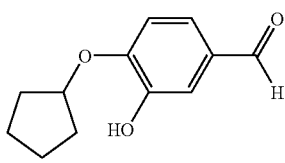
(B)

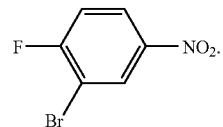
($B^1$)

The reaction is preferably performed in the presence of an alkali halide, such as potassium fluoride. The reaction is also preferably performed in a polar aprotic solvent.

Another aspect of the invention is a method for the preparation of 4-4-cyclopentyloxy-8-nitro-1-formyl dibenzo[b,d]furan (D) by cyclizing 4-cyclopentyloxy-3-(4'-nitro-2'-bromo phenoxy)-benzaldehyde (C)

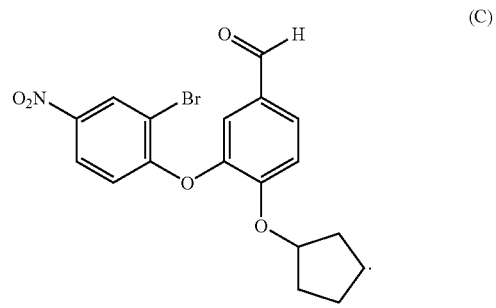
(C)

The benzaldehyde (C) may be prepared by reacting compounds (B) and ($B^1$) as discussed herein. The cyclization is preferably performed in the presence of palladium acetate. A suitable solvent for the reaction is dimethyl formamide.

Yet another aspect of the invention is a method for the preparation of a compound of formula (E-I)

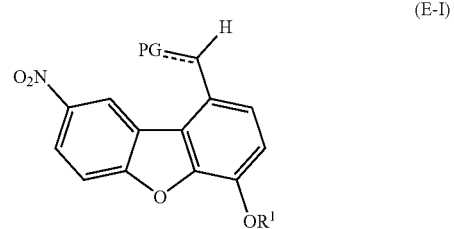
(E-I)

wherein $R^1$ is a hydrogen atom and PG is an aldehyde protecting group, by protecting 4-hydroxy-8-nitro-1-formyl dibenzofuran (E)

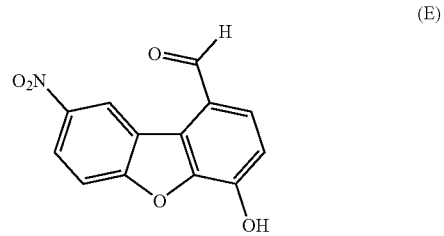
(E)

with an aldehyde protecting group. The dibenzofuran (E) may be prepared by any method described herein.

Yet another aspect of the invention is a method for the preparation of a compound of formula (E-Ib)

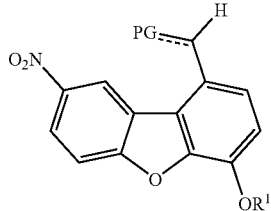
(E-Ib)

where $R^1$ is a substituted or unsubstituted $C_1$-$C_6$ alkyl and PG is an aldehyde protecting group, by alkylation of a compound of formula (E-I)

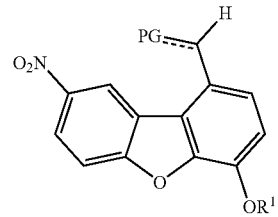
(E-I)

where $R^1$ is hydrogen and PG is as defined above. The dibenzofuran (E-I) may be prepared by any method described herein.

Yet another aspect of the invention is method for the preparation of a compound of formula (E-Ia)

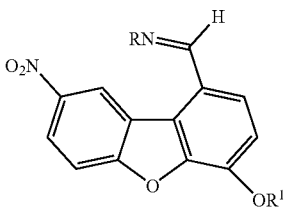
(E-Ia)

where
R is a substituted or unsubstituted alkyl, substituted or unsubstituted alkoxy, substituted or unsubstituted cycloalkyl, substituted or unsubstituted cycloalkylalkyl, substituted or unsubstituted aryl, substituted or unsubstituted arylalkyl, substituted or unsubstituted heteroaryl, substituted or unsubstituted heteroarylalkyl, substituted or unsubstituted heterocyclic group, or substituted or unsubstituted heterocyclylalkyl, and
$R^1$ is hydrogen,
by reacting 4-hydroxy-8-nitro-1-formyl dibenzofuran (E)

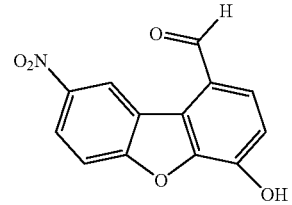
(E)

with an amine of the formula R—NH$_2$, where R is as defined above. The dibenzofuran (E) may be prepared by any method described herein.

Yet another aspect of the invention is a method for the preparation of a compound of formula (E-Ic)

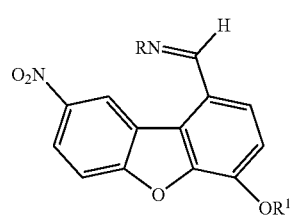
(E-Ic)

where
R is substituted or unsubstituted alkyl, substituted or unsubstituted alkoxy, substituted or unsubstituted cycloalkyl, substituted or unsubstituted cycloalkylalkyl, substituted or unsubstituted aryl, substituted or unsubstituted arylalkyl, substituted or unsubstituted heteroaryl, substituted or unsubstituted heteroarylalkyl, substituted or unsubstituted heterocyclic group, or substituted or unsubstituted heterocyclylalkyl, and
$R^1$ is a substituted or unsubstituted $C_{1-6}$ alkyl,
by alkylation of a compound of general formula (E-Ia)

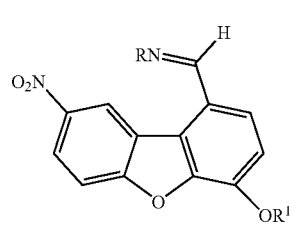
(E-Ia)

where $R^1$ is hydrogen and R is as defined above. The dibenzofuran (E-Ia) may be prepared by any method described herein.

Yet another aspect of the invention is a method for the preparation of 1-{[(4-methylphenyl)imino]methyl}-8-nitro-dibenzo[b,d]furan-4-ol ($E^1$)

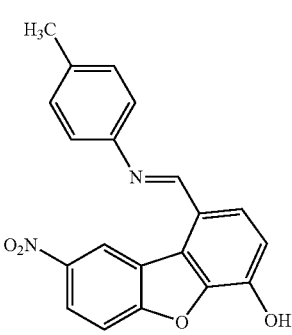
($E^1$)

by reacting 4-hydroxy-8-nitro-1-formyl dibenzofuran (E)

(E)
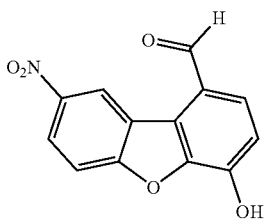

with 4-methyl aniline (p-toludine).

Yet another aspect of the invention is a method for the preparation of 1-{[(4-methylphenyl)imino]methyl}-4-difluoromethoxy-8-nitro-dibenzo[b,d]furan ($E^2$)

(E²)
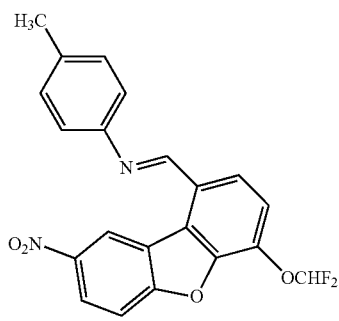

by reacting 1-{[(4-methylphenyl)imino]methyl}-8-nitro-dibenzo[b,d]furan-4-ol ($E^1$)

(E¹)
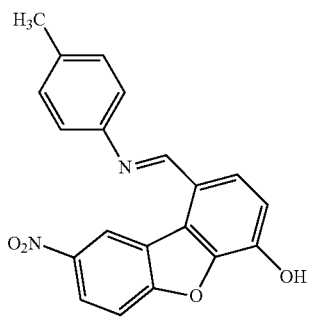

with $CHClF_2$.

Yet another aspect of the invention is a method for the preparation of p-nitrophenyl-4-difluoromethoxy-8-nitro dibenzofuran carboxylic acid ester (H) by reacting 4-difluoro-methoxy-8-nitro-dibenzofuran carboxylic acid (G) with para-nitro phenol ($G^1$)

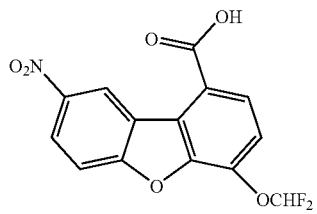 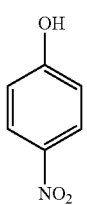

Preferably, the reaction is performed in the presence of thionyl chloride, and/or a suitable solvent.

Yet another aspect of the invention is a method for the preparation of N-(3,5-dichloropyrid-4-yl)-4-difluoromethoxy-8-nitrodibenzo[b,d]furan-1-carboxamide (I) by reacting p-nitrophenyl 4-difluoromethoxy-8-nitro-dibenzo[b,d]furan carboxylic acid ester (H) with 4-amino-3,5-dichloropyridine ($H^1$)

(H)
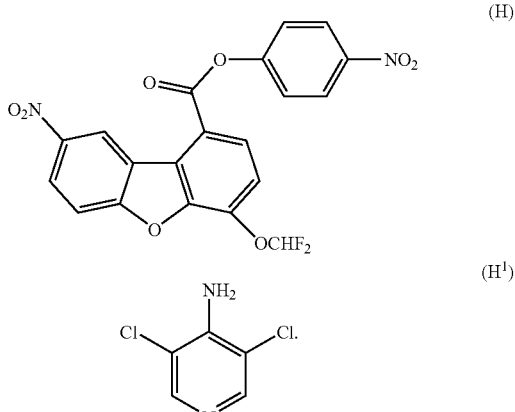

(H¹)

Preferably, the reaction is performed in the presence of a base, such as sodium hydride, and/or in a suitable solvent.

The intermediates formed in any of the aforementioned methods may be converted to N-(3,5-dichloropyrid-4-yl)-4-difluoromethoxy-8-methanesulfonamido-dibenzo[b,d]furan-1-carboxamide or a pharmaceutically acceptable salt thereof, such as its sodium salt, for example, by the methods described herein.

Yet another aspect of the invention is N-(3,5-dichloropyrid-4-yl)-4-difluoromethoxy-8-methanesulfonamido-dibenzo[b,d]furan-1-carboxamide or a pharmaceutically acceptable salt thereof prepared by any of the methods of the present invention.

Yet another aspect of the invention are the following novel intermediate compounds and salts thereof:

(i) 4-cyclopentyloxy-3-(4'-nitro-2'-bromo phenoxy)-benzaldehyde (C), (ii) a compound of the formula (E-I)
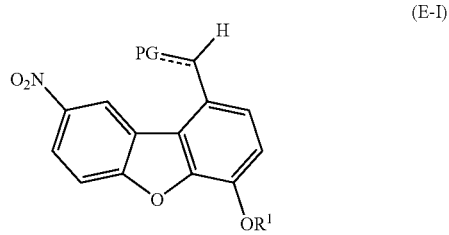

where
$R^1$ is hydrogen, and
PG is an aldehyde protecting group, (iii) a compound of the formula (E-Ib)
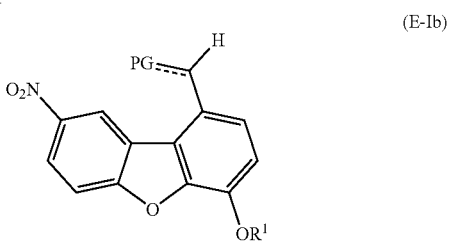

where
R¹ is a substituted or unsubstituted C₁₋₆ alkyl, and
PG is an aldehyde protecting group,
(iv) a compound of the formula

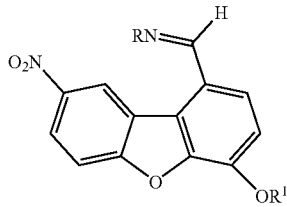

(E-Ia)

where
R is a substituted or unsubstituted alkyl, substituted or unsubstituted alkoxy, substituted or unsubstituted cycloalkyl, substituted or unsubstituted cycloalkylalkyl, substituted or unsubstituted aryl, substituted or unsubstituted arylalkyl, substituted or unsubstituted heteroaryl, substituted or unsubstituted heteroarylalkyl, substituted or unsubstituted heterocyclic group, substituted or unsubstituted heterocyclylalkyl, and
R¹ is hydrogen,
(v) a compound of the formula

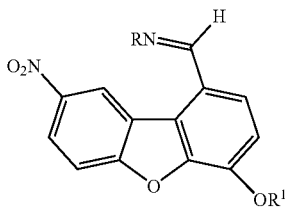

(E-1c)

where
R is a substituted or unsubstituted alkyl substituted or unsubstituted alkoxy, substituted or unsubstituted cycloalkyl, substituted or unsubstituted cycloalkylalkyl, substituted or unsubstituted aryl, substituted or unsubstituted arylalkyl, substituted or unsubstituted heteroaryl, substituted or unsubstituted heteroarylalkyl, substituted or unsubstituted heterocyclic group, substituted or unsubstituted heterocyclylalkyl, and
R¹ is substituted or unsubstituted C₁₋₆ alkyl,
(vi) 1-{[(4-methylphenyl)imino]methyl}-8-nitro-dibenzo[b,d]furan-4-ol (E¹),

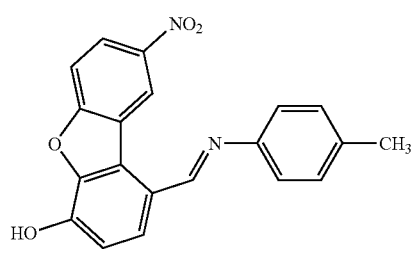

(E¹)

(vii) 1-{[(4-methylphenyl)imino]methyl}-4-difluoromethoxy-8-nitro-dibenzo[b,d]furan (E²),

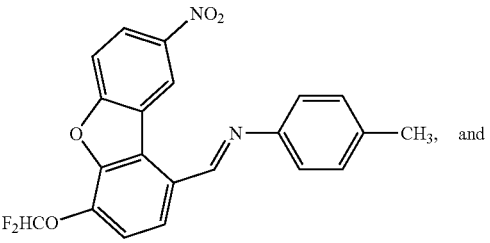

(E²)

(viii) p-nitrophenyl-4-difluoromethoxy-8-nitrodibenzo[b,d]furan-1-carboxylic acid ester (H)

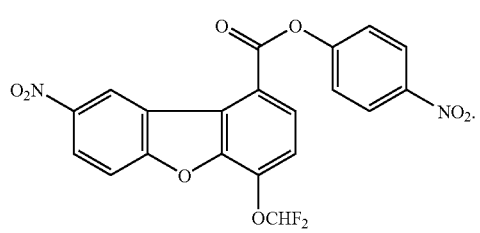

(H)

Preferred intermediate compounds, include intermediate (iii) (compounds E-Ia), where R is a substituted or unsubstituted aryl. Further preferred are compounds where R is 4-methylphenyl. Further preferred are compounds where R¹ is hydrogen. Further preferred are compounds where R¹ is a substituted or unsubstituted C₁₋₆ alkyl. Further preferred are compounds where R¹ is CHF₂.

Yet another aspect of the invention is a compound having the formula:

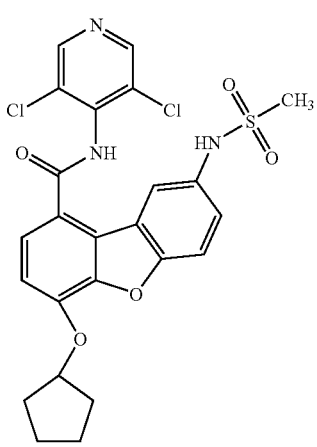

Compound L or a salt thereof.

Yet another aspect of the invention is a compound having the formula:

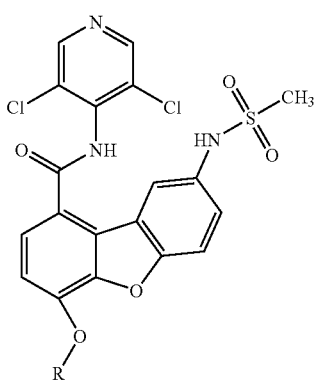

Compound L2 where R is cycloalkyl, or a salt thereof.

Yet another aspect of the invention is N-(3,5-dichloropyrid-4-yl)-4-difluoromethoxy-8-methanesulfonamido-dibenzo[b,d]furan-1-carboxamide or a pharmaceutically acceptable salt thereof having any one of the aforementioned intermediates, compound L, or compound L2 in an amount less than 0.2%, 0.15%, 0.1%, or 0.05% (based upon 100% total weight of N-(3,5-dichloropyrid-4-yl)-4-difluoromethoxy-8-methanesulfonamido-dibenzo[b,d]furan-1-carboxamide or its pharmaceutically acceptable salt thereof and the intermediate). According to one embodiment, the N-(3,5-dichloropyrid-4-yl)-4-difluoromethoxy-8-methanesulfonamido-dibenzo[b,d]furan-1-carboxamide or a pharmaceutically acceptable salt thereof has intermediate compound F, G, H, I, or J, compound L or compound L2 in an amount less than 0.2%, 0.15%, 0.1%, or 0.05%.

Yet another aspect of the invention is a pharmaceutical composition comprising N-(3,5-dichloropyrid-4-yl)-4-difluoromethoxy-8-methanesulfonamido-dibenzo[b,d]furan-1-carboxamide or a pharmaceutically acceptable salt thereof containing any one of the aforementioned intermediates, compound L, or compound L2 in an amount less than 0.2%, 0.15%, 0.1%, or 0.05% (based upon 100% total weight of N-(3,5-dichloropyrid-4-yl)-4-difluoromethoxy-8-methanesulfonamido-dibenzo[b,d]furan-1-carboxamide or its pharmaceutically acceptable salt thereof and the intermediate, compound L, or compound L2). Preferably, the pharmaceutical composition includes a pharmaceutically acceptable excipient, such as a carrier or diluent.

Yet another aspect of the invention is N-(3,5-dichloropyrid-4-yl)-4-difluoromethoxy-8-methanesulfonamido-dibenzo[b,d]furan-1-carboxamide or a pharmaceutically acceptable salt thereof (such as its sodium salt) having a purity of at least 98, 99, or 99.5%.

Yet another aspect of the invention is a pharmaceutical composition comprising N-(3,5-dichloropyrid-4-yl)-4-difluoromethoxy-8-methanesulfonamido-dibenzo[b,d]furan-1-carboxamide or a pharmaceutically acceptable salt thereof having a purity of at least 98, 99, or 99.5%.

Yet another aspect of the invention is a method of treating an allergic or inflammatory disease (including those disclosed in International Publication No. WO 2004/089940 and U.S. Patent Publication No. 2005-0027129, both of which are hereby incorporated by reference), such as asthma or COPD, by administering (i) N-(3,5-dichloropyrid-4-yl)-4-difluoromethoxy-8-methanesulfonamido-dibenzo[b,d]furan-1-carboxamide or a pharmaceutically acceptable salt thereof containing any one of the aforementioned intermediates in an amount less than 0.2%, 0.15%, 0.1%, or 0.05%, (ii) N-(3,5-dichloropyrid-4-yl)-4-difluoromethoxy-8-methanesulfonamido-dibenzo[b,d]furan-1-carboxamide or a pharmaceutically acceptable salt thereof having a purity of at least 98, 99, or 99.5%, or (iii) a pharmaceutical composition of the present invention.

DETAILED DESCRIPTION OF THE INVENTION

Definitions

An "aldehyde-protecting group" is a substituent attached to an aldehyde group that blocks or protects the carbonyl group of the aldehyde functionality in the compound. Suitable carbonyl protecting groups of the aldehyde functionality include, but are not limited to (a) cyclic acetals and ketals, (b) cyclic mono or di-thio acetals or ketals or other derivatives such as imines, hydrazones, cyanohydrin, oximes or semicarbazones, for example, dialkyl or diaryl acetals or 1,3 dithiane, (c) cyclic imines such as substituted methylene derivatives or N,N'-dimethylimidazolidine. For a general description of protecting groups and their use, see, T. W. Greene, Protective Groups in Organic Synthesis, John Wiley & Sons, New York, 1991 and T. W. Greene P. G. M. Wuts, Protective Groups in Organic Synthesis, 3rd edition John Wiley & Sons, Inc., 1999.

The term "alkyl" refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (isopropyl), n-butyl, n-pentyl, and 1,1-dimethylethyl (t-butyl).

The term "cycloalkyl" denotes a non-aromatic mono or multicyclic ring system of about 3 to 12 carbon atoms such as cyclopropyl, cyclobutyl, cyclopentyl, cyclohexyl and examples of multicyclic cycloalkyl groups include perhydronapththyl, adamantyl and norbornyl groups bridged cyclic group or sprirobicyclic groups e.g., sprio (4,4) non-2-yl.

The term "aryl" refers to aromatic radicals having in the range of 6 up to 14 carbon atoms such as phenyl, naphthyl, tetrahydronapthyl, indanyl, and biphenyl.

The term "heterocyclic ring" refers to a stable 3- to 15 membered ring radical which consists of carbon atoms and from one to five heteroatoms selected from the group consisting of nitrogen, phosphorus, oxygen and sulfur. For purposes of this invention, the heterocyclic ring radical may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heteroaromatic or heteroaryl aromatic). Examples of such heterocyclic ring radicals include, but are not limited to, azetidinyl, acridinyl, benzodioxolyl, benzodioxanyl, benzofurnyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazoyl, imidazolyl, tetrahydroisouinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxasolidinyl, triazolyl, indanyl, isoxazolyl, isoxasolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, furyl, tetrahydrofurtyl, tetrahydropyranyl, thienyl, benzothienyl, thiamorpholinyl, thiamorpholinyl sulfoxide thiamorpholinyl sulfone, dioxaphospholanyl, oxadiazolyl, chromanyl, and isochromanyl. The above includes substituted or unsubstituted pyridyl N-oxides.

The term "heteroaryl" refers to heterocyclic ring radical as defined above. The heteroaryl ring radical may be attached to the main structure at any heteroatom or carbon atom that results in the creation of a stable structure.

The term "halogen" includes radicals of fluorine, chlorine, bromine and iodine.

The terms "alkali halide salt" and "alkali halide" include, but are not limited, to, KF, KBr, KCL, KI, NaF, NaBr, NaCl, NaI, LiF, Cl, LiBr, and LiI.

The term "organic acid" includes, but is not limited to, carboxylic acids such as acetic acid, propionic acid, formic, trifluoroacetic, and paratoluene sulfonic.

The term "inorganic acid" includes, but is not limited to, mineral acids, HBr, phosphoric acid, HCl, HI, $H_2SO_4$ and Lewis Acids, such as $BF_3$, $BCl_3$, and $AlCl_3$.

The term "organic base" includes, but is not limited to, trialkyl amines, such as triethylamine and diisopropylamines, and heterocylic amines, such as imidazole, pyridine, pyridazine, pyrimidine, and pyrazine; anionic nitrogen bases, such as lithium diisopropylamide, and potassium bis(trimethylsilyamide), and bicyclic amines, such as DBN, and DBU.

The term "inorganic base" includes, but is not limited to, carbonates such as lithium carbonate sodium carbonate, sodium bicarbonate and cesium carbonate.

Suitable oxidants includes, but is not limited to, reagents such as potassium permanganate and chromium based oxidants such as the Jones Reagent ($CrO_3$ in sulfuric acid).

Suitable catalysts for the reduction step include, but are not limited to, suitable hydrogenation catalysts such as reactivated Raney Nickel, Pearlmans catalyst (palladium hydroxide), and Pd/C.

The term "palladium catalyst" includes, but is not limited to, Pd(II) complexes such as $Pd(OAc)_2$.

Pharmaceutically acceptable salts forming part of this invention include salts derived from inorganic bases such as Li, Na, K, Ca, Mg, Fe, Cu, Zn, Mn; salts of organic bases such as N,N'-diacetylethylenediamine, glucamine, triethylamine, choline, hydroxide, dicyclohexylaamine, metformin, benzylamine, trialkylamino, thiamine, and the like; chiral bases like alkylphenylamine, glycinol, phenyl glycinol and the like, salts of natural amino acids such as glycine, alanine, valine, leucine, isoleucine, norleucine, tyrosine, cystine, cysteine, methionine, proline, hydroxy proline, histidine, omithine, lysine, arginine, serine, and the like; quaternary ammonium salts of the compounds of invention with alkyl halides, alkyl sulphats like MeI, $(Me)_2SO_4$ and the like. Non-natural amino acids such as D-isomers or substituted amino acids; guanidine, substituted guanidine wherein the substituents are selected from nitro, amino, alkyl, alkenyl, alkynyl, ammonium or substituted ammonium salts and aluminum salts. Salts may include acid addition salts where appropriate which are, sulphates, nitrates, phosphates, perchlorates, borates, hydrohalides, acetates, tartrates, maleates, citrates, fumarates, succinates, palmoates, methanesulphonates, benzoates, salicylates, benzenesulfonates, ascorbates, glycerophosphates, ketoglutarates and the like. Pharmaceutically acceptable solvates may be hydrates or comprise other solvents of crystallization such as alcohols.

Salts can be obtained by dissolving the free compound in a suitable solvent, e.g., in a chlorinated hydrocarbon, such as methylene chloride or chloroform, or a low molecular weight aliphatic alcohol (e.g., ethanol and isopropanol) which contains the desired acid or base, or to which the desired acid or base is then added. The salts are obtained by filtering, reprecipitating, precipitating with a non-solvent for the addition salt or by evaporating the solvent. Salts obtained can be converted by basification or by acidifying into the free compounds which, in turn can be converted into salts.

The substances according to the invention are isolated and purified in a manner known per se, e.g. by distilling off the solvent in vacuum and recrystallizing the residue obtained from a suitable solvent or subjecting it to one of the customary purification methods, such as column chromatography on a suitable support material.

In general, organic solvents include, but are not limited to, the ethereal solvents described herein as well as chlorinated solvents, aromatic solvents, alcoholic solvents, diethyl ether, 1,2-dimethoxyethane, tetrahydrofuran, diisopropyl ether, and 1,4 dioxane. Suitable chlorinated solvents include, but are not limited to, dichloromethane, 1,2-dichloroethane, chloroform, and carbon tetrachloride. Suitable aromatic solvents include, but are not limited to, benzene and toluene. Suitable alchoholic solvents include, but are not limited to, methanol, ethanol, n-propanol, isopropanol, and tert-butanol. Sutiable polar aprotic solvents include, but are not limited to, N,N-dimethylformamide and dimethyl sulfoxide.

In general, the compounds prepared in the above described processes are obtained in pure form by using well known techniques such as crystallization using solvents such as pentane, diethyl ether, isopropyl ether, chloroform, dichloromethane, ethyl acetate, acetone, methanol, ethanol, isopropanol, water or their combinations, or column chromatography using alumina or silica gel and eluting the column with solvents such as hexane, petroleum ether (pe.t.ether), chloroform, ethyl acetate, acetone, methanol or their combinations.

Synthesis

In one embodiment N-(3,5-dichloropyrid-4-yl)-4-difluoromethoxy-8-methanesulfon amido-dibenzo[b,d]furan-1-carboxamide or a pharmaceutically acceptable salt thereof is synthesized by the method shown in scheme I below. In the scheme, Intermediate E can be converted to Intermediate F either directly by alkylation in the presence of $CHClF_2$ and $K_2CO_3$-DMF, or by protection of the aldehyde functionality by forming a Schiff base to provide ($E^1$) followed by alkylation of ($E^1$) in the presence of $CHClF_2$ and K2CO3-DMF to provide ($E^2$) which can then be subjected to deprotection (with or without isolation) using dilute HCl to give Intermediate F. This indirect conversion of Intermediate E to Intermediate F via $E^1$ and $E^2$ provides a significant improvement in the percentage yield of Intermediate F which in turn results in increased overall yield of N-(3,5-dichloropyrid-4-yl)-4-difluoromethoxy-8-methanesulfonamido-dibenzo[b,d]furan-1-carboxamide (or a pharmaceutically acceptable salt thereof) Intermediate F is then converted to the desired compound N-(3,5-dichloropyrid-4-yl)-4-difluoromethoxy-8-methanesulfonamido-dibenzo[b,d]furan-1-carboxamide or a pharmaceutically acceptable salt.

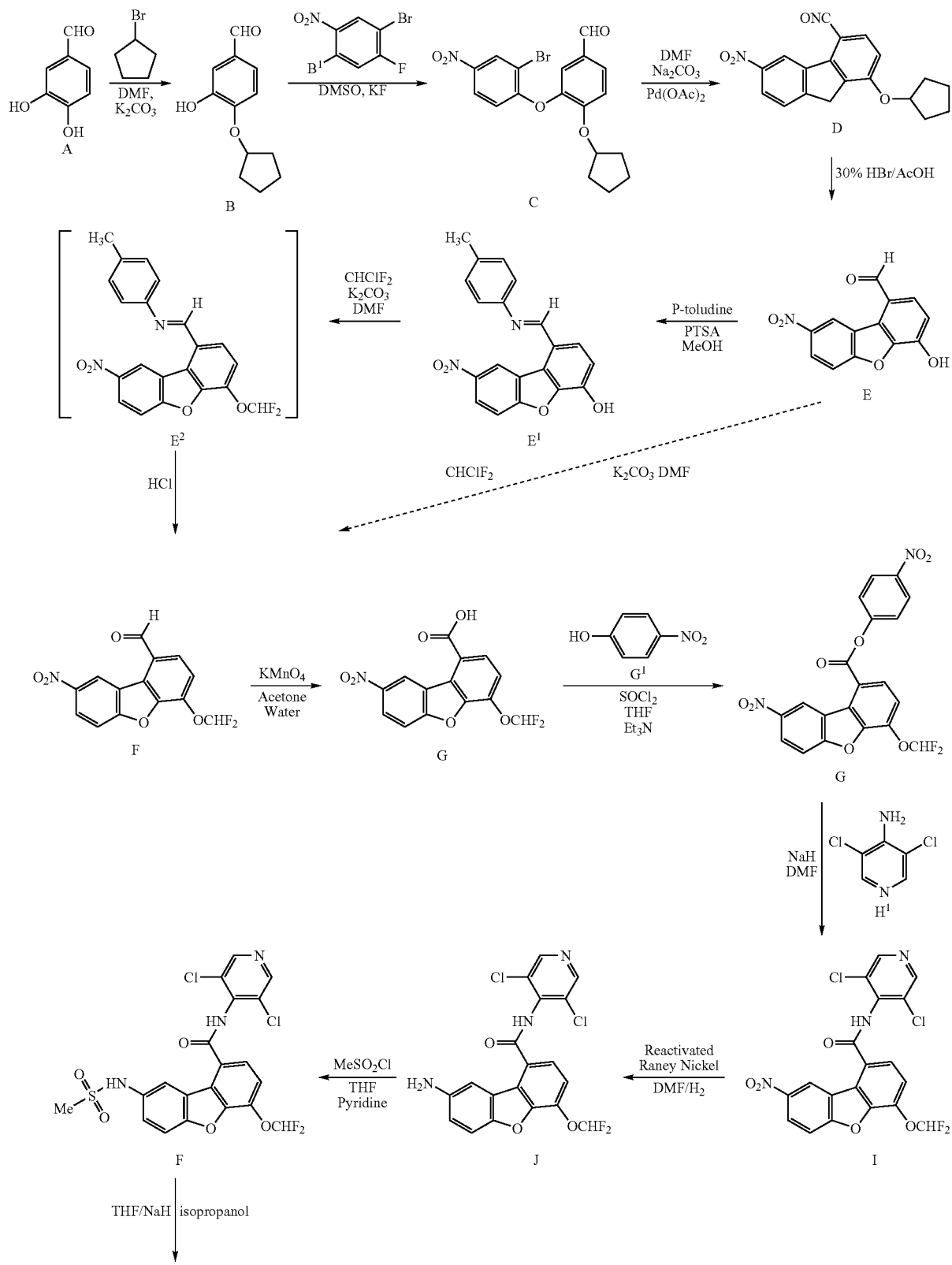

-continued
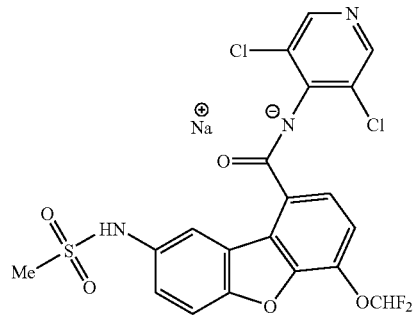
Compound L may be prepared by skipping the step of converting compound D to compound F, i.e., compound D is converted to an analog of compound G, where the —OCHF$_2$ substituent is replaced by a cyclopentyl group.
An alternative synthesis, Scheme IA, is provided below.
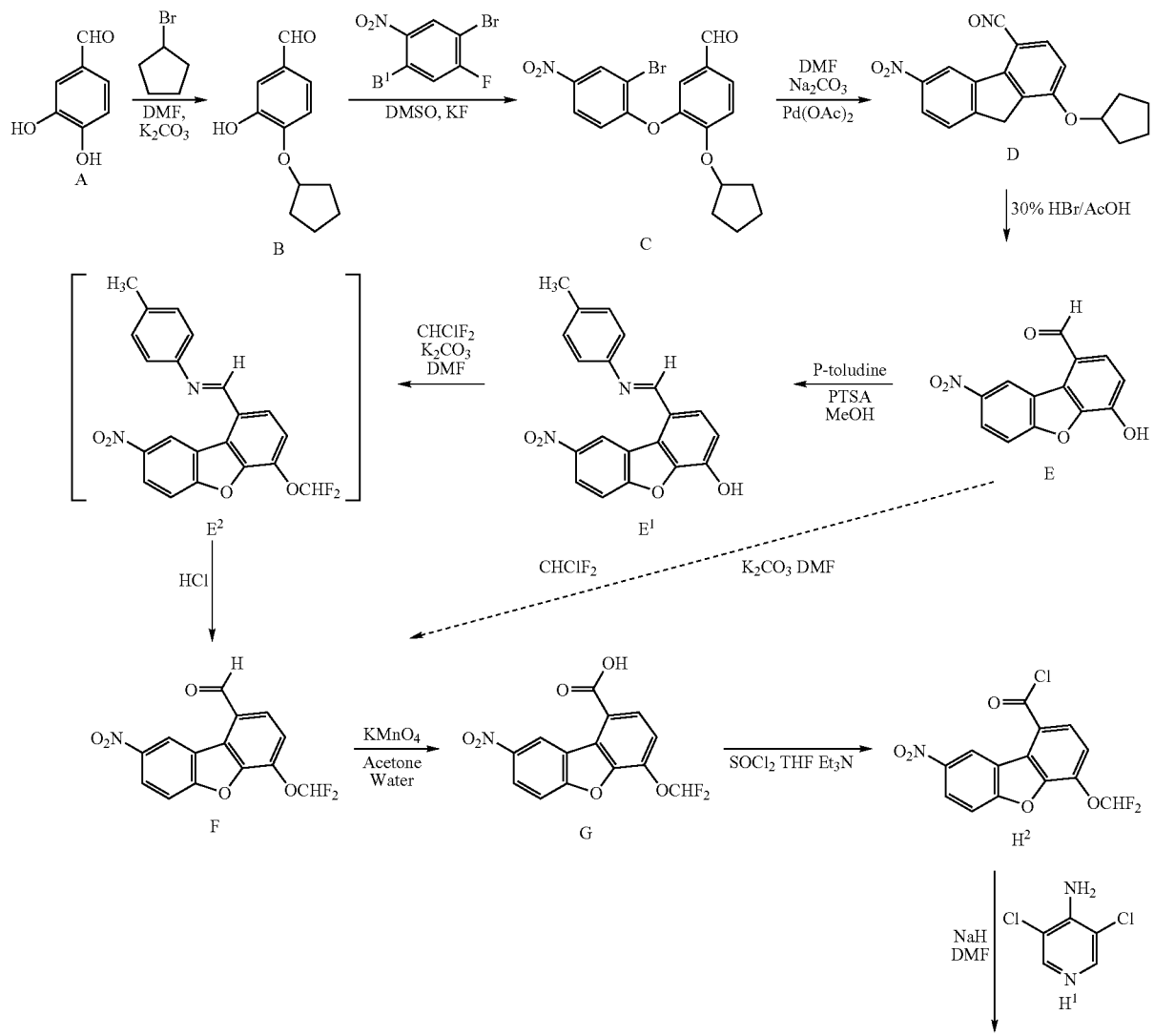

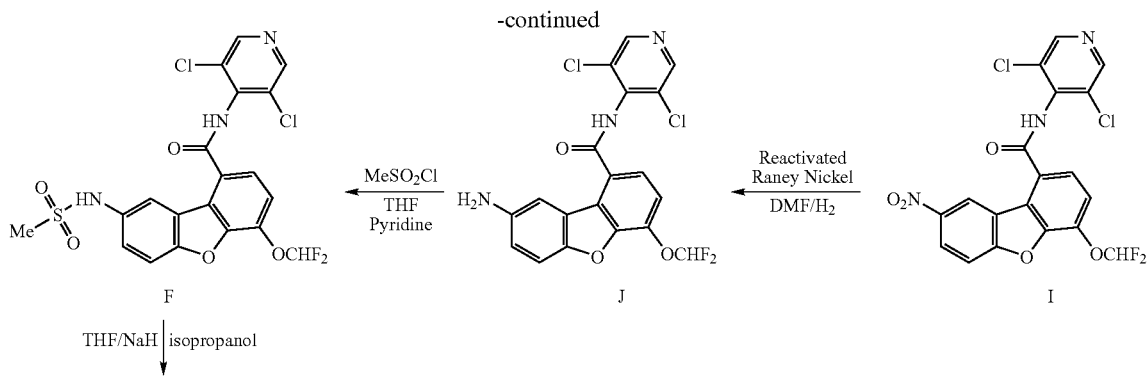

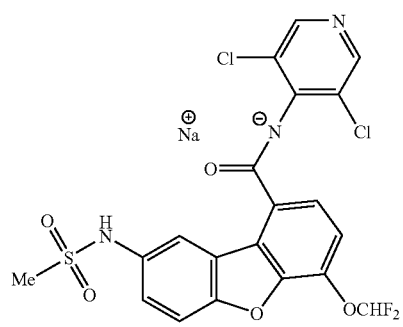

In Scheme IA, the hydroxyl group in the carboxylic acid moiety of compound G is converted to a halogen, such as Cl (Compound $H^2$). This conversion may be performed by reacting compound G with an acid halide, such as an acid chloride. Alternatively, the carboxylic acid group of compound G may be converted to an carboxyl activating group of the formula —C(O)L. The phrase "carboxyl activating group" is defined below.

Compound $H^2$ (and any compound prepared by converting the carboxylic acid group of compound G to a carboxyl activating group as discussed above) may be converted with compound $H^1$ to compound I as discussed in Scheme I above.

Compound L may be prepared by skipping the step of converting compound D to compound F, i.e., compound D is converted to an analog of compound G, where the —OCHF$_2$ substituent is replaced by a cyclopentyl group.

N-(3,5-dichloropyrid-4-yl)-4-difluoromethoxy-8-methanesulfonamido-dibenzo[b,d]furan-1-carboxamide or a pharmaceutically acceptable salt thereof can also be synthesized using the general method shown in scheme II below.

SCHEME II

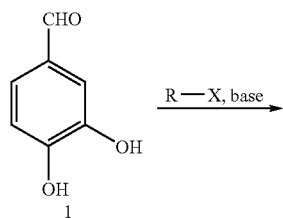

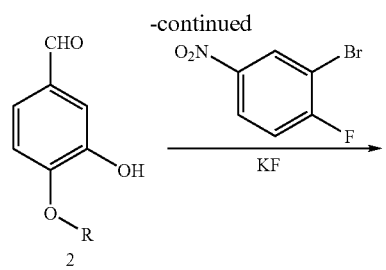

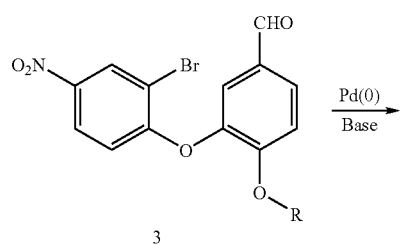

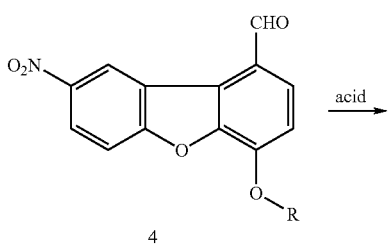

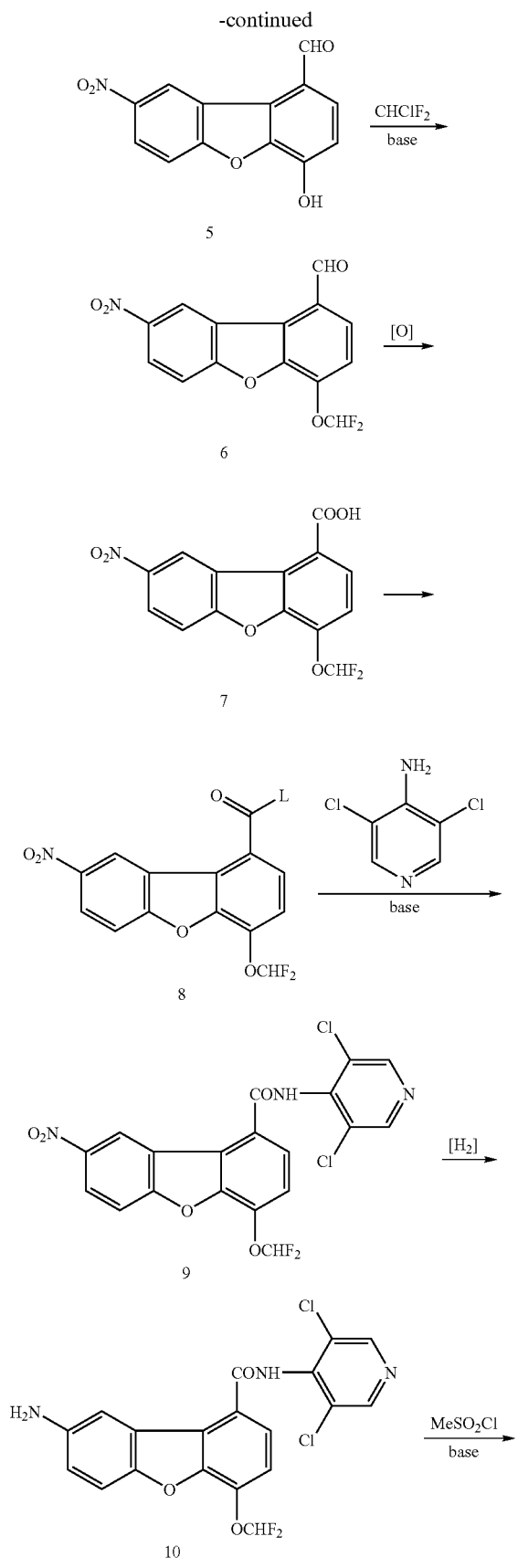

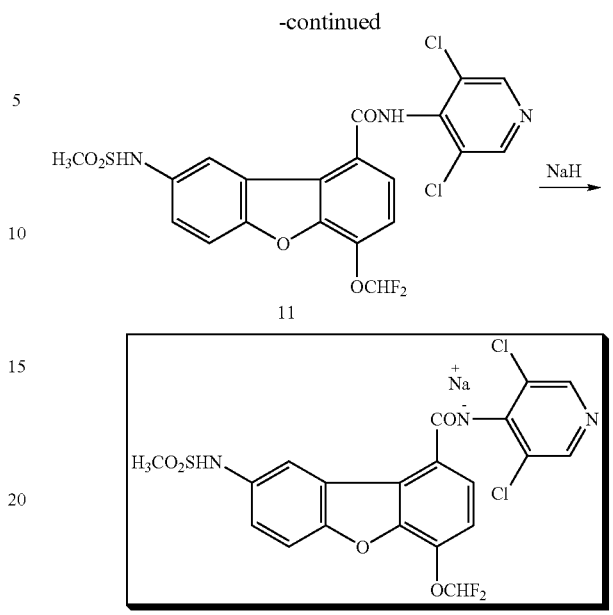

In the scheme II, 3,4-hydroxy benzaldehyde (1) is reacted with an alkyl or cycloalkyl halide to form an aryl ether of Formula 2. Preferably, 3,4-hydroxy benzaldehyde (1) is reacted with a cycloalkyl halide, such as a cyclopentyl halide. Preferably, the halide is bromo. The reaction is preferably performed in the presence of an inorganic or organic base, preferably $K_2CO_3$. The reaction is also preferably performed in a polar aprotic solvent (e.g., DMF).

Compound (2) is reacted with 2-bromo-1-fluoro-4-nitro benzene to yield the coupled product of Formula 3. Preferably, this reaction in performed in the presence of an alkali halide, such as KF. This reaction is also preferably performed in a polar aprotic solvent such as DMSO.

Compound (3) is cyclized to form compound (4). For example, Intramolecular cyclization of compound (3) can be performed using a palladium reagent, such as $Pd(OAc)_2$. Preferably, the cyclization is performed in the presence of an inorganic base, such as $Na_2CO_3$. This reaction is also preferably performed in a polar aprotic solvent, such as DMF.

The R group is then cleaved off compound (4) to form compound (5). For example, the ether linkage can be cleaved by treating compound (4) with an acid. Suitable acids include, but are not limited to, inorganic acids, organic acids, and mixtures thereof. A preferred acid mixture is HBr/AcOH.

Compound (5) is converted to compound (6), such as by reaction with $CHClF_2$. Preferably, this reaction is performed in the presence of an inorganic or organic base, such as $K_2CO_3$. This reaction is also preferably performed in a polar aprotic solvent, such as DMF.

Alternatively, compound (5) may be converted to compound (6) by (i) protecting the aldehyde group of compound (5), (ii) converting the hydroxyl group of the compound to —$OCHF_2$, such as by reaction with $CHClF_2$, and (iii) deprotecting the aldehyde group. Step (ii) is preferably performed in the presence of an inorganic or organic base, such as $K_2CO_3$. Step (ii) is also preferably performed in a polar aprotic solvent, such as DMF.

Compound (6) is oxidized, converting the aldehyde group to a carboxylic acid group, to form compound (7). The oxidation may be performed by treating compound (6) with an oxidizing reagent, such as KMnO$_4$. The oxidation may be performed in an aqueous organic solvent, such as acetone.

The carboxylic acid functionality of compound (7) is converted into an activated carboxyl group of the formula —C(O) L. This step yields the compound (8). The phrase "carboxyl activating group" refers to a moiety that replaces the hydrogen or hydroxyl of a carboxylic acid thereby altering the chemical and electronic properties of the carboxyl group such that the carboxyl group is more susceptible to nucleophilic attack or substitution. In embodiments in which the hydroxyl is replaced, exemplary carboxyl activating groups include chloro. In embodiments in which the hydrogen is replaced, exemplary carboxyl activating groups include electron deficient alkyl, aryl or heteroaryl groups, and phenyl group substituted with one or more electron withdrawing groups, such as halogen or nitro.

A non-limiting example of a suitable leaving group is chloro. Compound (8), where L is chloro, can be prepared by reacting a compound (7) with SOCl$_2$ in the presence of an organic base.

The group —C(O)-L can also be an ester derived from an electron deficient alcohol. For example, L can be an alkyl or aryl with one or more electron withdrawing groups. Compound (8), where L is alkyl or aryl with one or more election withdrawing groups, can be prepared by reacting compound 8 where L is chloro with an electron deficient alcohol to form compound (9). A suitable electron deficient alcohol is p-nitrophenol.

Compound (8) is coupled with 3,5 dichloro-4-amino pyridine to form compound (9). Preferably, compound (8) is reacted with 3,5 dichloro-4-amino pyridine in the presence of an organic or inorganic base, such as NaH. Preferably, the coupling reaction is performed in a polar aprotic solvent, such as DMF.

Alternatively, compound (9) may be prepared by directly coupling the carboxylic acid group of compound (7) to 3,5-dichloro-amino pyridine. For example, compound (7) and 3,5 dichloro-4-amino-pyridine may be reacted in the presence of a carbodimide and a catalyst to form compound (9). A non-limiting example of a suitable carbodimide is dicyclohexyl carbodimide. A non-limiting example of a suitable catalyst is dimethyl amino pyridine (DMAP).

Compound (9) is reduced to form compound (10). Preferably, the reduction reaction is performed with a catalyst, such as a reactivated Raney Nickel. The reduction can be performed in an alcoholic or polar aprotic solvent, such as DMF. According to one embodiment, the reaction is performed in the presence of hydrogen. The reduction can also be performed under phase transfer hydrogenation conditions.

Compound (10) is reacted with methane sulfonyl chloride to form compound (11). This reaction can be performed in the presence of an inorganic or organic base, such as pyridine. This reaction can also be performed in an organic solvent, such as THF.

The sulfonamide of Formula 11 is optionally converted to a pharmaceutically acceptable salt thereof. For example, the sulfonamide can be converted to its sodium salt by the action of NaH in an organic solvent.

Compounds L and L2 may be prepared by skipping the step of converting compound 4 to compound 6, i.e., compound 4 is converted to an analog of compound 7, where the —OCHF$_2$ substituent is replaced by a cyclopentyl group. Compound 4 may be oxidized, converting the aldehyde group to a carboxylic acid group, to form the analog of compound (7). The oxidation may be performed by treating compound (4) with an oxidizing reagent, such as KMnO$_4$. The oxidation may be performed in an aqueous organic solvent, such as acetone.

Specifically, the synthesis of N-(3,5-dichoropyrid-4-yl)-4-difluoromethoxy-8-methane sulfonamido-dibenzo[b,d]furan-1-carboxamide and its corresponding sodium salt can be synthesized using the method in Scheme III below.

SCHEME III

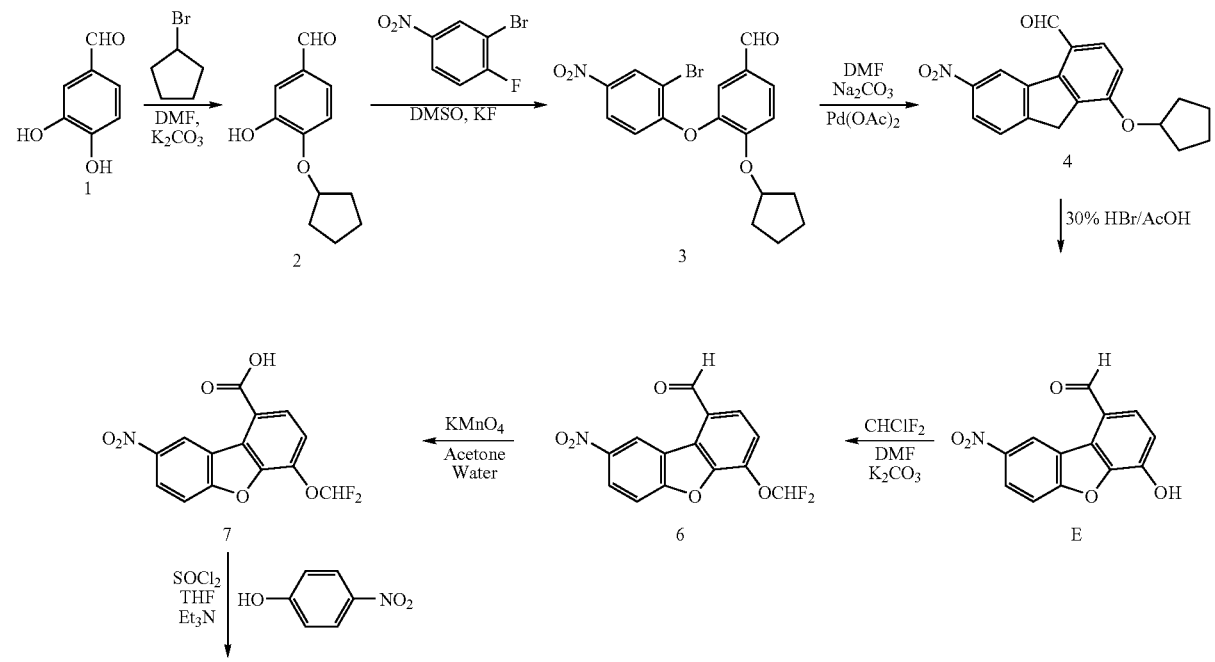

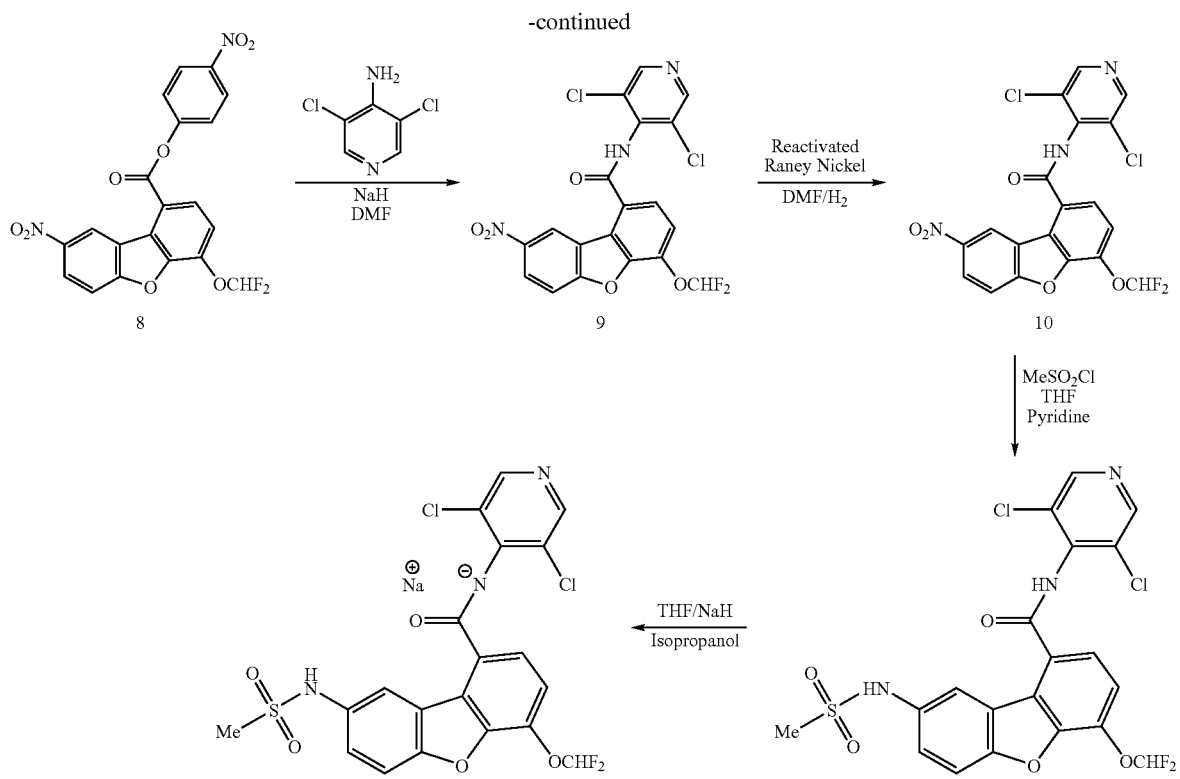

In the above mentioned scheme a dihydroxybenzaldehyde compound 1, is 3,4 dihydroxy benzaldehyde 1 is reacted with cyclopentyl bromide in the presence of $K_2CO_3$ in DMF to afford a compound of the Formula 2. The cyclopentyl derivative is then reacted with 2-bromo-1-fluoro-4-nitro benzene in the presence of KF in DMSO to afford the compound of Formula 3. Intramolecular cyclization of Formula 3 is accomplished using $Pd(OAc)_2$ in the presence of $Na_2CO_3$ in DMF to afford the cyclized produce of Formula 4. Formula 4 is then subjected to 30% HBr in AcOH to afford Formula 5. Formula 5 is then reacted with chlorodifluoromethane in the presence of $K_2CO_3$ in DMF to afford the product of the Formula 6. Formula 6 is then oxidized using potassium permanganate in acetone water to afford a compound of Formula 7. Formula 7 is then reacted with thionyl chloride in the presence of triethylamine in THF to form the corresponding acid chloride which is then reacted in situ with p-nitrophenol to afford the compound of Formula 8. Formula 8 is then reacted with 4-amino-3,5-dichloropyridine in the presence of sodium hydride in DMF to afford the compound of Formula 9. Formula 9 is then reduced using Reactivated Raney Nickel in the presence of hydrogen in DMF to afford the compound of Formula 10. Formula 10 is then reacted with methane sulfonyl chloride in the presence of pyridine in THF to afford the title compound which is converted into its corresponding sodium salt by the action of sodium hydride in THF/isopropanol.

Compounds L and L2 may be prepared by scheme III by skipping the step of converting compound 4 to compound 6, i.e., compound 4 is converted to an analog of compound 7, where the —$OCHF_2$ substituent is replaced by a cyclopentyl group. Compound 4 may be oxidized, converting the aldehyde group to a carboxylic acid group, to form the analog of compound (7). The oxidation may be performed by treating compound (4) with an oxidizing reagent, such as $KMnO_4$. The oxidation may be performed in an aqueous organic solvent, such as acetone.

Other alternative reagents to those disclosed in Schemes I-III are described in International Publication No. WO 2004/089940 and U.S. Patent Publication No. 2005-0027129, both of which are hereby incorporated by reference.

It will be appreciated that some of the compounds of the invention defined above according to the invention can contain one or more asymmetrically substituted carbon atoms. The presence of one or more of these asymmetric centers in the compounds of the invention can give rise to stereoisomers and in each case the invention is to be understood to extend to all such stereoisomers, including enantiomers and diastereomers and their mixtures, including racemic mixtures. The invention may also contain E and Z geometrical isomers wherever possible in the compounds of the invention which includes the single isomer or mixture of both the isomers The pharmaceutical compositions may be in the forms normally employed, such as tablets, capsules, powders, syrups, solutions, and suspensions, and may contain flavorants and sweeteners in suitable solid or liquid carriers or diluents, or in suitable sterile media to form injectable solutions or suspensions. The active compounds of the invention will be present in such pharmaceutical compositions in the amounts sufficient to provide the desired dosage in the range as described above. Thus, for oral administration, the compounds of the invention can be combined with a suitable solid, liquid carrier or diluent to form capsules, tablets, powders, syrups, solutions, suspensions and the like. The pharmaceutical compositions, may, if desired, contain additional components such as flavorants, sweeteners, excipients and the like. For parenteral administration, the compounds of the invention can be combined with sterile aqueous or organic media to form injectable solutions or suspensions. For example, solutions in sesame or peanut oil, aqueous propylene glycol and the like can be used as well as aqueous solutions of water-soluble pharmaceutically-acceptable acid addition salts or salts with base of the compounds of the invention The injectable solutions prepared in this manner can then be administered intravenously, intraperitoneally, subcutaneously, or intramuscularly, with intramuscular administration being preferred in humans.

The compounds can also be administered by inhalation when application within the respiratory tract is intended. Formulation of the present compounds is especially significant for respiratory inhalation, wherein the compound of the invention is to be delivered in the form of an aerosol under pressure. It is preferred to micronize the compound of the invention after it has been homogenized, e.g., in lactose, glucose, higher fatty acids, sodium salt of dioctylsulfosuccinic acid or, most preferably, in carboxymethyl cellulose, in order to achieve a microparticle size of 5 μm or less for the majority of particles. For the inhalation formulation, the aerosol can be mixed with a gas or a liquid propellant for dispensing the active substance. An inhaler or atomizer or nebulizer may be used. Such devices are known. See, e.g., Newman et al., Thorax, 1985, 40:61-676; Berenberg, M., J. Asthma USA, 1985, 22:87-92; incorporated herein by reference in their entirety. A Bird nebulizer can also be used. See also U.S. Pat. Nos. 6,402,733; 6,273,086; and 6,228,346, incorporated herein by reference in their entirety. The compound of the invention for inhalation is preferably formulated in the form of a dry powder with micronized particles. The compounds of the invention may also be used in a metered dose inhaler using methods disclosed in U.S. Pat. No. 6,131,566, incorporated herein by reference in its entirety.

In addition to the compounds of the invention, the pharmaceutical compositions of the present invention may also contain or be co-administered with one or more known drugs selected from other clinically useful therapeutic agents.

The invention is explained in detail in the examples given below which are provided by way of illustration only and therefore should not be construed to limit the scope of the invention.

EXAMPLE 1

4-Cyclopentyloxy-3-hydroxybenzaldehyde

In a 10 L 4 necked RB flask fitted with a mechanical stirrer, reflux condenser, was added DMF (3.5 L), 3,4-Dihydroxybenzaldehyde (1.15 Kg, 8.3M), cyclopentyl bromide (3.1 kg, 20.3 M) and powdered anhydrous potassium carbonate (1.15 kg, 20.3 M) at temperature in the range of 25-35° C. under stirring. The reaction mixture was heated to temperature of 75-80° C. under stirring and maintained under stirring for 1 hr. To the reaction mixture, powdered potassium carbonate (140 g, 1M) was added at temperature of 75-80° C. under stirring. After addition, the reaction mixture was maintained at 75-80° C. for 1 hr. The progress of the reaction was monitored by TLC and HPLC. After ascertaining the completion of the reaction, the reaction mixture was brought to 25-35° C. and filtered. The inorganic salt cake was washed with DMF (300 ml×2) and combine the washings with filtrate. The organic layer was concentrated at temperature below 75° C. under high vaccum. Add toluene (2 L) to the residue of distil of the residual DMF. Add toluene (2 L) to the resulting mass and distill off the traces of DMF. To the resulting mass, add toluene (5.7 L), celite (300 g), activated charcoal (100 g), 5% sodium hydroxide solution (1.2 L) and cool to 10-15° C. under stirring. Separate the organic and aqueous layer. The organic layer was repeatedly extracted with 5% sodium hydroxide solution (1.2 L×5) and combine the aqueous sodium hydroxide layers. The aqueous layer was washed with toluene (2 L×2) and separate the aqueous layer. The pH of the aqueous layer was adjusted to acidic 2-3 with conc. HCl (1.1 L) at 10-15° C. under stirring. The precipitated solid was filtered, washed with water(2 L×3) filtered and dried in the hot air oven below 60° C. temp. The product appear as cream color solid, weighing about 920-950 g, yield 54%-56% purity 98-99%, m.p 87-89° C. The IR (KBr) spectrum shows 3300 (OH str), 3150 (CH str), 1670 (CHO str), 1620 (C=C str). The 1H-NMR (DMSO-d6) shows δ 9.8 (s, 1H), 9.2 (s, 1H), 7.1 (d, 1H), 7.2-7.4 (m, 2H), 4.9 (m, 1H), 1.4-2.0 (m, 8H). The CI mass shows m/z 206 (M+). The elemental analysis shows calculated % C, 69.88; % H, 6.84; % O, 23.27; observed % C, 69.70; % H, 6.65; % O, 23.15.

EXAMPLE 2

2-bromo-1-fluoro-4-nitro benzene

In a 20 L 4-necked RB flask, fitted with a mechanical stirrer, reflux condenser, add DM water (550 ml), conc. Sulphuric acid (6.2 L, 113 M), 4-fluronitrobenzene(1.0 kg, 7.09 M) at 25-35° C. under stirring. The reaction mixture was cooled to 10° C. and bromine (1.13 kg, 7.06 M) was added to reaction mixture under stirring. The reaction mixture was brought to temp. 25-35° C., silver sulfate (1.1 kg, ~3.53 M) was added in one portion to the reaction mixture at 25-35° C. and maintained for 30-32 h under stirring. Monitor the progress of the reaction by GC and after ascertaining completion, the reaction mixture was poured slowly into ice cold water (12 L) and dichloromethane (12 L) mixture. Filter the insoluble and wash the inorganic with dichloromethane (2 L). Combine the organic layer, wash with 10% sodium bicarbonate (3 L), water (5 L). The dichloromethane layer was distilled below 40° C. under vacuum and add n-Hexane (4.5 L) to the residue. The resulting mass was stirred at 25-35° C. for 4-5 hr, filter the product and dried in vacuum oven below 35° C. till LOD reaches <1%. The dried product appears as white lustrous crystalline solid, weighs about 1.1-1.2 kg, yield 70-77%, purity 97-98% by HPLC, m.p. 56-58° C. The structure assigned to the product is in agreement with spectral data.

EXAMPLE 3

4-Cyclopentyloxy-3-(4'-nitro-2'-bromophenoxy) benzaldehyde

In a 20 L 4-necked RB flask, fitted with a mechanical stirrer, reflux condenser, add dimethyl sulfoxide (4.5 L) 4-cyclopentyloxy-3-hydroxybenzaldehyde (900 g, 4.36 M) potassium fluoride (510 g, 8.5 M), 2-bromo-1-fluoro-4-nitro benzene (970 g, 4.38M) at temperature 25-35° C. under stirring. The reaction mixture was heated to 95-100° C. and maintained for 18-20 h under stirring. The reaction mixture was cooled to temperature of 25-35° C. and water (4.5 L) was added to the reaction mixture and maintained for 2 h under stirring. The precipitated product was filtered, washed with water(3 L×3), 5% sodium hydroxide solution (2 L×2), water (5 L×4), finally with n-Hexane(4.5 L×2). The product was dried in vacuum. Oven at 55-60° C. till MC reaches <1 %. The dried product appears as pale yellow solid, weight 1.689 kg-1.7 kg, yield 70-77%, m.p 95-96° C., purity 97-98% by HPLC, m.p. 92-94° C. The IR (KBr) spectrum shows 3150 (CH str), 2960 (CH str), 1682 (CHO str), 1340 (NO2 str). The 1H-NMR (DMSO-d6) shows δ 9.8 (s, 1H), 8.8 (s, 1H), 8.2 (d, 1H), 7.8-8.0 (m, 2H), 7.4 (d, 1H) 6.8 (d, 1H) 5.0 (m, 1H), 1.2-1.8 (m, 8H). The CI mass shows m/z 406 (M+). The elemental analysis shows calculated % C, 53.22; % H, 3.97; % N, 3.46; observed % C, 53.10; % H, 3.86; % N, 3.35.

EXAMPLE 4

4-Cyclopentyloxy-8-nitro-1-formyl dibenzofuran

In a 20 L 4 necked RB Flask, fitted with a mechanical stirrer, reflux condenser, add 4-cyclopentyloxy-3(4'-nitro-2'-bromophenoxy)benzaldehyde (1.3 kg, 3.20 M), dimethyl formamide (7.8 L), sodium carbonate (0.51 kg, 4.8M) at temperature in the range of 25-35° C. under stirring. Heat the reaction mixture to temperature of 130-140° C. and add palladium acetate. Trimer (75 g, 0.11M) and maintain at temperature of 130-140° C. for 1 h under stirring. After 1 hr maintenance, the second lot of palladium acetate trimer (75 g, 0.11M) was added at temperature of 130-140° C. under stirring and maintained for 1 hr. After 2 hr maintenance the third lot of palladium acetate trimer (75 g, 0.11M) was added at temperature of 130-140° C. under stirring and maintained for 1 hr. The progress of the reaction mixture was monitored by HPLC. The reaction mixture was cooled to 70° C. and 4.7 L of THF was added to the reaction mixture and stirred for 30 min. The inorganic insolubles were filtered and washed with THF (1 L×2). Collect the THF MLS and add to DM water (15 L) under stirring. The precipitated product was filtered, washed with water (5 L) and dried in the vacuum oven at temp. below 60° C. The dried product was subjected to reflux in a mixture of THF (1.3 L) and Ethyl acetate (2.6 L) for 2 h and brought to room temperature. The precipitated product was filtered, dried in oven at temp. below 60° C. under vaccum till MC reaches <1%. The dried product appears as pale yello solid, weighs about 650-700 g, yield 60-65%, purity 97-98% by HPLC, m.p. 230-232° C. The IR (KBr) spectrum shows 3120 (CH str), 2960 (CH str), 1682 (CHO str), 1340 (NO2 str)

The 1H-NMR (DMSO-d6) shows δ 10.2 (s, 1H), 9.8 (s, 1H), 8.4 (d, 1H), 8.2-7.8-(dd, 2H), 7.4 (d, 1H), 5.2 (m, 1H), 1.6-2.2 (m, 8H). The CI mass shows m/z 325 (M+). The elemental analysis shows calculated % C, 66.46; % H, 4.65; % N, 4.31; observed % C, 66.35; % H, 4.51; % N, 4.25.

EXAMPLE 5

4-hydroxy-8-nitro-1-formyldibenzofuran

In a 20 L 4 necked RB flask fitted with a mechanical stirrer, reflux condenser, add 4-cyclopentyloxy-8-nitro-1-formyldibenzofuran (1.2 kg, 3.75 M), 30% Hydrobromic acid in acetic acid (6 L) under stirring. Heat the reaction mixture to 80-90° C. and maintain for 30 min under stirring. Additional quantity of 30% Hydrobromic acid in acetic acid (4.2 L×3 times) was added lot wise in the interval of every 45 minutes at temp. 80-90° C. The progress of the reaction was monitored by HPLC. It was observed that that 2-3% of the starting material was left un reacted, even after prolonging the maintenance for additional 1hr. After this, the reaction mixture was cooled to 10-15° C. and water (24 L) was added at 10-15° C. under stirring. The diluted reaction mixture was brought to 25-35° C. and maintained for 30 min under stirring. The precipitated product was filtered, washed with water (8 L×5) till pH becomes neutral. The wet cake was charged with toluene (12 L) and subjected to azeotropic distillation of water by refluxing to temperature of 110° C. After complete removal of water, the reaction mixture was brought to 25-35° C. filtered and dried in vaccum oven below 60° C. till MC/LOD reaches <1%. The dried product appears as pale yellow solid, weighs about 896-915 g, yield 93-95%, purity 97% by HPLC, m.p>270° C. The product was further purified as follows. In a 10 L four necked RB flask, fitted with a mechanical stirrer, reflux condenser add 4-hydroxy-8-nitro-1-formyldibenzofuran obtained in the above step (1.0 kg, 3.89 M), dimethyl foramide (2 L) at 25-35° C. under stirring. The RM was heated to 80° C. and maintained for 30 min under stirring for complete dissolution. After dissolution, potassium carbonate (850 g, 6.11 M) was added at 80° C. and maintained for 2 h under stirring. The reaction mixture was cooled to 10° C. and filtered. The wet cake was washed with acetone (1 L) and the solid after washing was dissolved in DM water (9 L) and the solution was cooled to 5-10° C. under stirring. The pH of the aqueous solution was adjusted from 10 to 4.5 by neutralizing with conc. HCl (1.5 L). The precipitated product was filtered washed with water (10 L×5) till pH becomes neutral, dried in vacuum. Oven at 60-65° C. till MC<1%. The dried product appears as cream solid, weighs about 800-820 g, yield 83%-85%, m.p.>270; purity>99% by HPLC. The IR (KBr) spectrum shows 3130 (CH str), 1657 (CO str), 1333 (NO2 str) The 1H-NMR (DMSO-d6) shows δ 12.0 (broad, 1H), 10.2 (s, 1H), 9.8 (s, 1H), 8.6 (d, 1H), 8.0 (m, 2H), 7.2 (d, 1H). The CI mass shows m/z 257 (M+). The elemental analysis shows calculated % C, 60.71; % H, 2.74; % N, 5.45; observed % C, 60.59; % H.

EXAMPLE 6

4-difluoro methoxy-8-nitro-1-formyl dibenzo(b,d)furan

Method A

In a 10 L 4 necked RB flask fitted with a mechanical stirrer, reflux condenser, add 4-hydroxyl-8-nitro-1-formyl-dibenzo (b,d)furan (700 g, 2.72 M), dimethyl formamide (4.2 L) at temp. 25-35° C. under stirring. The reaction mixture was heated to 80-90° C. under stirring and potassium carbonate (1.126 kg, 8.1M) was added at 80-90° C. under stirring. Chlorodifluoromethane gas was bubbled into the reaction mixture at 80-90° C. for 3-4 hr while monitoring the HPLC at every 1 hr interval of time. After ascertaining the completion of the reaction by HPLC, bring the RM to 25-35° C. and filter the inorganic salts. The inorganic salts cake was washed with DMF(600 ml×2) and collect, combine all the washings. The combined DMF layer was distilled below 90° C. under high vacuum. DM water (1.6 L) was added to the residue and the pH of the aqueous solution was adjusted to pH 4-5 with conc. HCl (40 ml. The precipitated product was filtered, washed with DM water (400 ml×2) and suck dried. The wet cake was subjected to azeotropic removal of water by refluxing in toluene (7 L) at temperature of 100-110° C. After complete removal of water, the reaction mixture was brought to 25-35° C. under stirring and the insoluble solid was filtered. The insoluble cake was washed with toluene (400 ml×2). Collect all the washings and combine for distillation. The combined toluene layer was concentrated below, 70° C. under vacuum. The precipitated product was filtered washed with toluene (1 L) and dried in vaccum oven at temp. below 60° C. The dried product appears as cream color solid, weighs about 393-410 g, yield 50-52%, purity~95% by HPLC, m.p. 245-248° C. The IR(KBr) spectrum shows 3120 (CH str), 2950 (CH str), 1690 (CHO str), 1340 (No2 str) cm-1. The 1H-NMR (DMSO-d6) shows δ 10.2 (s, 1H), 9.8 (s, 1H), 8.6 (d, 1H), 8.2 (d, 1H), 8.2 (d, 1H), 7.4-7.8 (m, 3H) The CI mass shows m/z 307 (M+). The elemental analysis shows calculated % C, 54.7; % H, 2.30; % N, 4.56; observed % C, 54.5; % H, 2.15; % N, 4.40.

Method B

Step I: Synthesis of 1-{(4-Methylphenyl)imino]methyl-}8-nitrodibenzo-[b,d]furan-4-ol: The reactor (capacity ?) was charged with 4-hydroxyl-8-nitro-1-formyl-dibenzo(b,d)furan (10 Kg, 0.52 M )and Methanol (200 L) and stirred for 15 min. Then p-toluidine (12.5 Kg. 116.82 M) and PTSA (0.1 Kg, 0.52 M) was added to the reactor at temp. 25-35° C. under stirring. The reaction mixture was heated to 65-70° C. Reaction was monitored by TLC and HPLC. Reaction was complete in 4-5 h. Methanol was distilled out from reaction mixture below 50° C. under vacuum. Hexane was charged to the reaction mass and stirred for 30 min at 35° C. Reaction mass was cooled to 25-30° C. and stirred for 1 h. Reaction mass was filtered and solid was washed with hexane (10 L). Solid was spin dried for 1 h and then at 50° C. for 5 h. Yield=12.0-13.0 Kg, Purity=98% by HPLC. The 1H-NMR (DMSO-d6) shows δ 11.3 (s, 1H), 10.8 (s, 1H), 9.0 (s, 1H), 8.5 (d, 1H), 8.0 (d, 1H), 7.8 (d, 1H), 7.2-7.5 (m, 5H), 2.4)(s, 3H).

Step II: Preparation of 4-difluoro methoxy-8-nitro-1-formyl dibenzo(b,d)furan: The reactor was charged with DMF (120 L) and 1-{(4-Methylphenyl)imino]methyl-}8-nitrodibenzo[b,d]furan-4-ol (10.0 Kg) and stirred for 15 min. Then Potassium carbonate (7.97 Kg, 57.66 M) was added to the reactor and stirred for 15 min at 25-30° C. Chlorodifluoromethane gas was bubbled into the reaction mixture at 60° C. for 3-4 hr while monitoring the HPLC at every 1 hr interval of time. After ascertaining the completion of the reaction by HPLC, bring the RM to 25-35° C. and filter the inorganic salts through hyflo-bed. The inorganic salts cake was washed with DMF(600 ml×2) and collect, combine all the washings. The combined DMF layer was distilled below 60° C. under high vacuum (upto 15 L volume) to yield a crude mass of 1-{(4-Methylphenyl)imino]methyl-}4-difluoro methoxy-8-nitrodibenzo[b,d]furan.

Step III: The above crude residue of 1-{(4-Methylphenyl)imino]methyl-}4-difluoro methoxy-8-nitrodibenzo[b,d]furan was cooled to 25-30° C. and add conc. HCl (50 ml) stir for 15 mins. Then add Methanol (10 L) and water (50 L) to the reaction mass. Heat the reaction mass to 60° C. and check the completion of hydrolysis by TLC and HPLC. Reaction was complete in 2-3 h. After completion of reaction, the reaction mass was cooled to 40° C. The precipitated product was filtered, washed with DM water till pH is 7.0. The wet cake was subjected to spin dry for 1 h and dried at 60° C. for 8 h under vacuum. Yield=8 Kg, purity~98% by HPLC. NMR (DMSO-d6) shows δ 10.2 (s, 1H), 9.8 (s, 1H), 8.6 (d, 1H), 8.2 (d, 1H), 7.4-7.8 (m, 3H).

EXAMPLE 6a

1-{(4-Methylphenyl)imino]methyl-}4-difluoro methoxy-8-nitrodibenzo[b,d]furan

The compound was synthesized using the process as described in Step I and Step-II of Method B followed by purification to provide 1-{(4-Methylphenyl)imino]methyl-}4-difluoro methoxy-8-nitrodibenzo[b,d]furan.

$^1$H NMR (δ ppm): 2.4 (3H, s), 7.3-8.1 (8H), 8.4 (1H, dd), 9.0 (1H, s), 10.3 (1H, d).

EXAMPLE 7

4-difluoromethoxy-8-nitrodibenzo[b,d]furan-1-carboxylic acid

In a 20 L 4 necked RB flask, fitted with a mechanical stirrer, reflux condenser, add 4-difluoro methoxy-8-nitro-1-formyl dibenzo[b,d]furan (1 kg, 3.25 M), acetone (7.2 L) and heat to temp. 70-75° C. under stirring. Add a slurry of potassium permanganate (0.48 kg) in water (3 L) to the reaction mixture at 70-75° C. under stirring and maintain for 1 hr. After 1 hr maintenance, the second lot of potassium permanganate (0.120 kg) in water (400 ml) was added at 70-75° C. under stirring and maintain for 1 hr. After 2 hr maintenance, the third lot of potassium permanganate (0.120 kg) in water (400 ml) was added at 70-75° C. under stirring and maintain for 1 hr. The progress of the reaction was monitored by HPLC. After ascertaining the completion of the reaction, acetone (7.2 L) was added at temp. of 70-75° C. under stirring and maintained for 30 min. The reaction mixture was brought to 25-35° C., filtered. The inorganic salt cake was washed with acetone (2 L) collect and combine all the acetone washings. The acetone MLS were distilled at temp. below 75° C. under vacuum, cool the residue to 25-35° C. and maintain under stirring for 30 min. The precipitated product was filtered, dried and the wet cake was subjected to reflux with a solvent mixture of (5 L acetone and 1.25 L water) and maintained for 3 h. Cool the reaction mass to 10-15° C. maintain for 30 min under stirring, filter the precipitated product, wash the product with water (1 L). The wet cake was subjected to azeotropic removal of water by refluxing with toluene (10 L) After complete removal of water, the reaction mixture was brought to 25-35° C., maintained for 30 min, filtered and dried in vacuum oven below 70° C. till LOD<1%. The dried product appears as cream color, solid, weighs about 840-850 g, yield 80-81%, purity~95% by HPLC, m.p.>270° C. The IR (KBr) spectrum shows 3100 (C—H str), 1695 (—COOH str), 1100 (C—F str) cm-1. The 1H-NMR spectrum shows δ 9.8 (s, 1H), 8.6 (d, 1H), 8.2 (m, 2H), 7.3 (m, 3H), 7.6 (m, 1H). The CI mass shows m/z 322 (M+) The elemental analysis shows calculated % C, 52.03; % H, 2.18; % N, 4.33. Observed % C, 52.04; % H, 2.03; % N, 4.45%.

EXAMPLE 8

P-nitrophehyl 4-difluormethoxy-8-nitro dibenzofuran carboxylic acid ester

In a 20 L 4-necked RB flask, filled with a mechanical stirrer, reflux condenser, add 4-difluoromethoxy-8-nitrobenzo[b,d]furan-1-carboxylic acid (1.0 kg, 3.09 M), thionyl chloride (3.0 L, ~4.86 kg, 40 M) at temp. 25-35° C. under stirring. The reaction mixture was heated to 80-90° C. and maintained for 3 h. The progress of the reaction was monitored by TLC. After ascertaining completion of the reaction, distil off thionyl chloride under vacuum below 70° C. The traces of thionyl chloride were removed completely by adding toluene (5 L×3) and distill off. To the residue THF (13 L), a suspension of p-nitrophenol (403 g in THF 2 L), triethyl amine (620 g, 6.13M) were added under stirring at 25-35° C. The reaction mixture was maintained at 25-35° C. for 5-6 hr while monitoring the progress of the reaction by HPLC. After ascertaining the completion of the reaction, ice cold water (15 L) was added to the reaction mixture maintained for 30 min under stirring at 25-35° C. The precipitated product was filtered, washed with water (10 L×5), methanol (1 L), suck dried. The wet cake was subjected to leaching at 90-95° C. with ethylene glycol monoethyl ether (5.0 L) for 3-4 hr. The reaction mixture was brought to 25-35° C., cooled to 5-10° C. under stirring, filter and dried at below 70° C. under vaccum till LOD reaches <1%. The dried product appears as cream color solid, weighs about 800-850 g, yield 58-62%, m.p.>270° C., purity 98% by HPLC. The IR (KBr) spectrum shows 3140 (C—H str), 1740 (CO str), 1346 (NO2 str), 1103

(C—F str) cm−1 The 1H-NMR spectrum shows (DMSO-d6) shows δ 9.6 (s, 1H), 8.4-8.6 (m, 4H), 8.1-8.2 (m, 2H), 7.6-7.8 (m, 4H) The CI Mass shows m/z 444 (M+). The elemental analysis shows calculated % C, 54.07; % H, 2.27; % N, 6.31; observed % C, 53.93; % H, 2.20; % N 5.94.

EXAMPLE 9

N'-(3,5 dichloropyrid-4-yl)-4-difluoromethoxy-8-Nitro dibenzo[b,d]furan-1-carboxamide In a 20 L 4 necked RB flask, fitted with a mechanical stirrer, reflux condenser, add p-ntrophenyl 4-difluoromethoxy-8-nitro dibenzofuran carboxylic acid ester (700 g, 1.56M) DMF (4 L), a suspension of 4-amino-3,5-dichloropyridine (307 g, 1.88M) in DMF (1 L) at temp. 25-35° C. under stirring. The reaction mixture was maintained at 25-35° C. for 20-25 min. Cool the reaction mixture to 0-5° C. under stirring for 30 min, 60% sodium hydride (125 g, 3.26 M) was added at 0-5° C. After addition the reaction mixture was brought to 25-35° C. and maintained 1 h. The progress of the reaction was monitored by HPLC. After ascertaining completion of the reaction by HPLC, the reaction mixture was cooled to 10-15° C. and 40% brine solution (500 ml), ice cold water (5 L) was added to the reaction mixture slowly and maintained for 10 min. 10% HCl (1.5 L) was added to the reaction mass till pH becomes 4.5-5.5 and maintained at pH 4.5-5.5 for 30 min. The precipitated product was filtered, washed with water (5 L×4). The wet cake was subjected to leaching at temp. 85-90° C. with ethylene glycol mono ethyl ether (3.5 L) for 8-10 hr under stirring. The reaction mixture was brought to 25-35° C., filter, wash the cake with diethylene glycol monoethyl ether (700 ml) and dried in vacuum. Oven below 70° C. till MC<1%. The dried product appears as cream color solid, weighs about 650-670 g, yield 86-90%, purity 98%, m.p.>270° C. The IR (KBr) spectrum shows 3146 cm−1 (CH, str) 1674 cm−1 (CONH str) 1340 (NO2 str) The 1H NMR (DMSO d6) spectrum shows δ 8.0 (s, 1H), 7.6 (s, 1H), 8-9 (s, 1H), 8.2 (s, 2H), 8.0 (s, 1H), 7.6 (s, 1H), 7.3 (s, 1H). The CI mass spectrum shows m/z 468 (M+). The elemental analysis shows calculated % C, 48.74%; % H, 1.94; % N, 8.97; observed % C, 48.64%; % H, 1.86; % N, 8.76.

EXAMPLE 10

N1-(3,5-dichloro pyrid-4-yl)-4-difluoromethoxy-8-amino dibenzo[b,d]furan-1-carboxanide In a 10 Lt autoclave, add N1-(3,5-dochloropyrid-4-yl)-4-difluoromethoxy-8-aminodibenzo[b,d]furan-1-carboxamide (600 g, 1.36M), DMF (4.8 L) and reactivated Raney Nickel (250 g) at 25-35° C. under stirring. The reaction mixture was hydrogenated with Hydrogen gas at a pressure of 5-6 kg/cm−2 for 5-6 h. The progress of the reaction was monitored by HPLC. After completion of the reaction, the reaction mixture was filtered and the Nickel cake was washed with DMF (500 ml). The DMF washings were collected, combined and distilled below 70° C. under vaccum. The residue was diluted with water (10 L), filter the precipitated product, washed the product cake with DM water(5 L×2), dry the product. The dried product appears as cream color solid, weighs about 540-550 g, yield 91-92%, m.p.>270° C., purity 98% by HPLC. The IR (KBr) spectrum shows 3450 (NH str), 3180 (CH str), 1670 (CONH str) cm−1. The 1H NMR (DMSO-d6) shows δ 11 (s, 1H), 9.0 (s, 1H), 8.2 (s, 2H), 7.6-7.7 (m, 1H), 7.3-7.4 (m, 3H). The CI mass show m/z 438 (M+). The elemental analysis shows calculated % C, 52.08%; % H, 2.53; % N, 9.59. Observed % C, 52.0%; % H, 2.30; % N, 9.86.

EXAMPLE 11

N1-(3,5-dichloropyrid-4-yl)-4-difluoromethoxy-8-(methanesulfonamide)-dibenzo[b,d]furan-1-carboxamide In a 20 Lt 4 necked RB flask fitted with a mechanical stirrer, reflux condenser, add N1-(3,5-dichloropyrid-4-yl)-difluoromethoxy-8-amino-dinebzo[b,d]furan-1-carboxamide (500 g, 1.14 M), THF (5 L), pyridine (1 L) at temperature 25-35° C. under stirring in about 30 min. The reaction mixture was maintained at 25-35° C. for 6 h. Monitor the progress of the reaction by HPLC. After ascertaining completion of the reaction, ice cold water (10 L) was added to the reaction mixture and maintained under stirring for 30 min. The precipitated product was filtered, washed with 5% HCl (5 L), water (5 L×2) and suck dried. The wet cake was subjected to leaching at 70-80° C. by refluxing with methanol (5 L) for 12 hrs. The reaction mixture was brought to 25-35° C. maintained for 30 min and filtered. The wet cake was washed with MeOH (500 ml) and dried in vacuum. Oven below temp. 70° C. The dried product appears as cream color solid, weighs about 530-540 g, yield 90-92%, purity 98% by HPLC, m.p.>270° C. The IR (KBr) 3320 (N—H str) 1698 (CONH str) 1277 (SO2 str), 1100 (CH str ) cm−1. The 1H-NMR (DMSO-d6), δ 9-7 (s, 1H), 8-9-9.0 (s, 1H), 8.2 (s, 2H), 8.0 (d, 1H), 7.6-7.7 (2h, 1H), 7.3-7.4 (m, 3H) 2.8 (s, 3H). The CIMS shows m/z 516 (M+); The elemental analysis shows calculated % C, 46.53; % H, 2.54; % N, 8.14; observed % C, 46.43; % H, 2.45; % N, 7.84.

EXAMPLE 12

N1-(3,5-dichloropyridine-4-yl)-4-(difluoromethoxy)-8-methane sulfonamide]dibenzo[b,d]furan-1-carboxamide sodium salt In a 10 Lt 4 necked RB flask fitted with a mechanical stirrer, reflux condenser, add N1-(3,5-dichloropyridine-4-yl)-(difluoromethoxy)-8-methanesulfonamido]dibenzo[b,d]furan-1-carboxamide (225 g, 0.43M), THF (2.2 L) under nitrogen atmosphere and stirring. The reaction mixture was cooled to 0-5° C. and 60% sodium hydride (19.2 g, 0.48 M) was added portion wise in about two hours. After the addition was completed the reaction mixture was maintained for 10 min at 5-10° C. and brought to 25-30° C. under stirring. THF (500 ml) was added to the reaction mixture and heated to 40-45° C. maintained for 30 min. Filter the reaction mixture and collect the THF MLS. To the THF MLS, charcoal (45 g) made as slurry in THF (250 ml) was added under stirring and maintained at 40-45° C. under stirring for 30 minutes. To the THF MLS, charcoal (45 g) made as a slurry in THF (250 ml) was added under stirring and maintained at 40-45° C. under stirring for 30 minutes To the THF MLS, charcoal (45 g) made as a slurry in THF (250 ml) was added under stirring and maintained at 40-45° C. under stirring for 30 minutes Filter the reaction mixture, separate the THF MLS, collect and combined. The combined THF MLS were distilled below 70° C. Isopropanol (1.3 L) was added to the residue under stirring, maintain under reflux for 8 h. The reaction mixture was cooled to 25-35° C., filter, wash with isopropanol (200 ml) and dried in the vacuum. Oven below 70° C. The dried product as pale yellow solid, weighs about 210-220 g, yield 90-95%, purity 98% by HPLC. The IR (KBr) spectrum shows 3094 (NH str), 3100 (C—H str), 1674 (CONH str), 1277 (SO2). Cm−1. The 1H-NMR (DMSO-d6) shows δ 9.7 (s, 1H), 8.9-9.0 (s, 1H), 8.2 (s, 2H), 8.0 (1H, d), 7.6-7.7 (m, 1H) 7.3-7.4 (m, 3H) 2.8 (s, 3H,). The 13C NMR (DMSO-d6) shows δ164.6, 155.9, 153, 146.8, 146.6, 135.7, 135.6, 134.6, 127.2, 125.2, 124.9, 122.3, 121.7, 120.3, 113.4, 116.7, 116.8, 111.5, 39.0. The CI mass spectrum shows m/z, 514 (M+). The elemental analysis shows calculated % C, 44.63; % H, 2.25; % N, 7.81; observed % C, 44.77; % H, 2.28; % N, 7.70.

All references, patents, and patent applications referred to herein are incorporated by reference.

We claim:

1. A method for the preparation of 4-cyclopentyloxy-3-(4'-nitro-2'-bromo phenoxy)-benzaldehyde (C) which comprises the step of reacting 4-cyclopentyloxy-3-hydroxy-benzaldehyde (B) with 3-bromo-4-fluoro nitrobenzene ($B^1$)

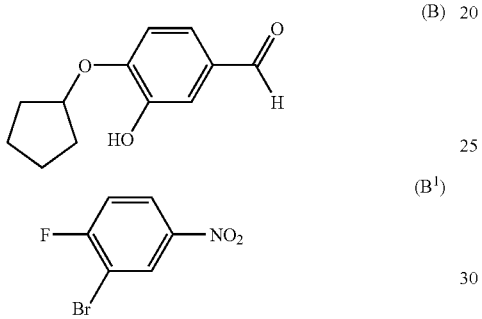

to yield 4-cyclopentyloxy-3-(4'-nitro-2'-bromo phenoxy)-benzaldehyde (C).

2. The method of claim 1, wherein the reaction is performed in the presence of an alkali halide.

3. The method of claim 2, wherein the alkali halide is potassium fluoride.

4. The method of claim 1, wherein the reaction is performed in a polar aprotic solvent.

5. The method of claim 1, which further comprises converting 4-cyclopentyloxy-3-(4'-nitro-2'-bromo phenoxy)-benzaldehyde (C) to N-(3,5-dichloropyrid-4-yl)-4-difluoromethoxy-8-methanesulfonamido-dibenzo[b,d]furan-1-carboxamide or a pharmaceutically acceptable salt thereof.

6. A method for the preparation of 4-cyclopentyloxy-8-nitro-1-formyl dibenzo-furan (D) which comprises the step of cyclizing 4-cyclopentyloxy-3-(4'-nitro-2'-bromo phenoxy)-benzaldehyde (C)

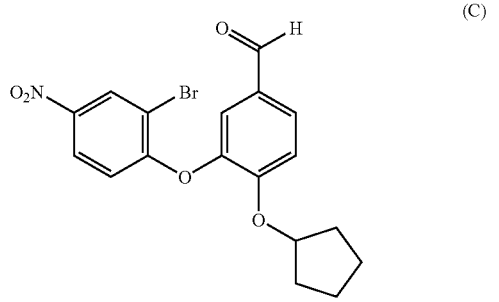

to yield 4-cyclopentyloxy-8-nitro-1-formyl dibenzofuran (D).

7. The method of claim 6, wherein the cyclization is performed in the presence of palladium acetate.

8. The method of claim 6, wherein the cyclization is performed in dimethyl formamide.

9. The method of claim 6, which further comprises converting 4-cyclopentyloxy-8-nitro-1-formyl dibenzofuran (D) to N-(3,5-dischloropyrid-4-yl)-4-difluoromethoxy-8-methanesulfonamido-dibenzo[b,d]furan-1-carboxamide or a pharmaceutically acceptable salt thereof.

10. A method for the preparation of a compound of formula (E-I)

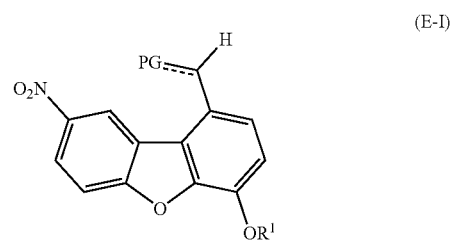

wherein $R^1$ is a hydrogen atom and PG is an aldehyde protecting group, the method comprising protecting 4-hydroxy-8-nitro-1-formyl dibenzofuran (E)

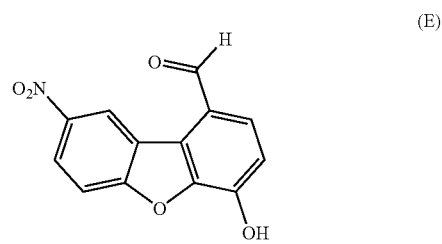

with an aldehyde protecting group to yield a compound of formula (E-I).

11. The method of claim 10, which further comprises converting the compound of formula (E-I) to N-(3,5-dichloropyrid-4-yl)-4-difluoromethoxy-8-methanesulfonamido-dibenzo[b,d]furan-1-carboxamide or a pharmaceutically acceptable salt thereof.

12. A method for the preparation of a compound of formula (E-Ib)

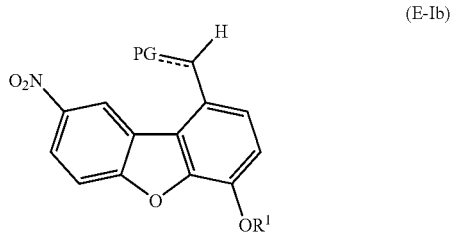

where $R^1$ is a substituted or unsubstituted $C_1$-$C_6$ alkyl and PG is an aldehyde protecting group, which comprises the step of alkylation of a compound of formula (E-I)

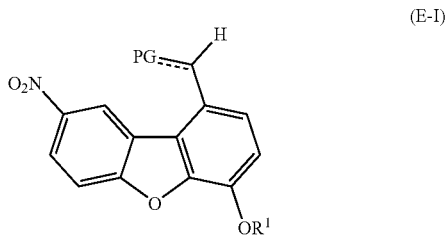

(E-I)

where $R^1$ is hydrogen and PG is as defined above, to yield a compound of formula (E-Ib).

13. The method of claim 12, which further comprises converting the compound of formula (E-Ib) to N-(3,5-dichloropyrid-4-yl)-4-difluoromethoxy-8-methanesulfon amido-dibenzo[b,d]furan-1-carboxamide or a pharmaceutically acceptable salt thereof.

14. A method for the preparation of a compound of formula (E-Ia)

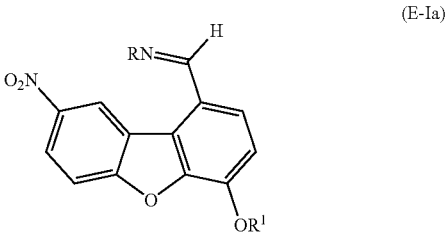

(E-Ia)

where
R is a substituted or unsubstituted alkyl, substituted or unsubstituted alkoxy, substituted or unsubstituted cycloalkyl, substituted or unsubstituted cycloalkylalkyl, substituted or unsubstituted aryl, substituted or unsubstituted arylalkyl, substituted or unsubstituted heteroaryl, substituted or unsubstituted heteroarylalkyl, substituted or unsubstituted heterocyclic group, or substituted or unsubstituted heterocyclylalkyl, and
$R^1$ is hydrogen,
which comprises the step of reacting 4-hydroxy-8-nitro-1-formyl dibenzofuran (E)

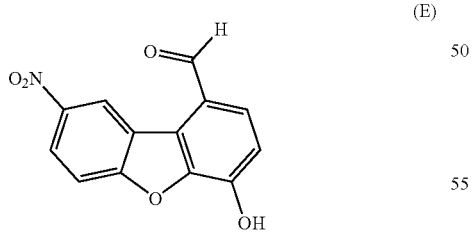

(E)

with an amine of the formula R—NH$_2$, where R is as defined above, to yield a compound of formula (E-Ia).

15. The method of claim 14, which further comprises converting a compound of formula (E-Ia) to N-(3,5-dichloropyrid-4-yl)-4-difluoromethoxy-8-methanesulfon amido-dibenzo[b,d]furan-1-carboxamide or a pharmaceutically acceptable salt thereof.

16. A method for the preparation of a compound of formula (E-Ic)

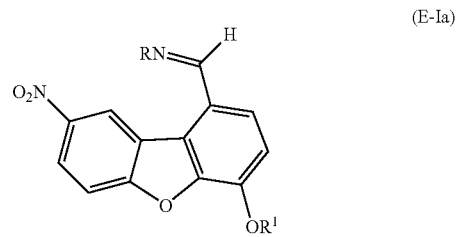

(E-Ic)

where
R is substituted or unsubstituted alkyl, substituted or unsubstituted alkoxy, substituted or unsubstituted cycloalkyl, substituted or unsubstituted cycloalkylalkyl, substituted or unsubstituted aryl, substituted or unsubstituted arylalkyl, substituted or unsubstituted heteroaryl, substituted or unsubstituted heteroarylalkyl, substituted or unsubstituted heterocyclic group, or substituted or unsubstituted heterocyclylalkyl, and
$R^1$ is a substituted or unsubstituted $C_{1-6}$ alkyl,
which comprises the step of alkylation of a compound of formula (E-Ia)

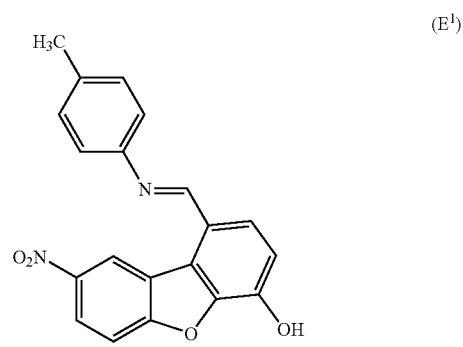

(E-Ia)

where $R^1$ is hydrogen and R is as defined above, to yield a compound of formula (E-Ic).

17. The method of claim 16, which further comprises converting the compound of formula (E-Ic) to N-(3,5-dichloropyrid-4-yl)-4-difluoromethoxy-8-methanesulfon amido-dibenzo[b,d]furan-1-carboxamide or a pharmaceutically acceptable salt thereof.

18. A method for the preparation of 1-{[(4-methylphenyl)imino]methyl}-8-nitro-dibenzo[b,d]furan-4-ol ($E^1$)

($E^1$)

which comprises the step of reacting 4-hydroxy-8-nitro-1-formyl dibenzofuran (E)

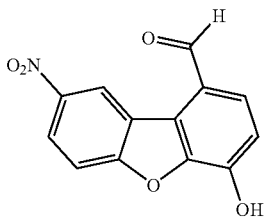
(E)

with 4-methyl aniline (p-toludine) to yield 1-{[(4-methylphenyl)imino]methyl}-8-nitro-dibenzo[b,d]furan-4-ol (E¹).

19. The method of claim 18, which further comprises converting 1-{[(4-methyl phenyl)imino]methyl}-8-nitro-dibenzo[b,d]furan-4-ol (E¹) to N-(3,5-dichloropyrid-4-yl)-4-difluoromethoxy-8-methanesulfonamido-dibenzo[b,d]furan-1-carboxamide or a pharmaceutically acceptable salt thereof.

20. A method for the preparation of 1-{[(4-methylphenyl)imino]methyl}-4-difluoromethoxy-8-nitro-dibenzo[b,d]furan (E²)

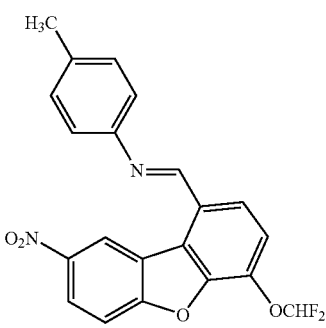
(E²)

which comprises the step of reacting 1-{[(4-methylphenyl)imino]methyl}-8-nitro-dibenzo[b,d]furan-4-ol (E¹)

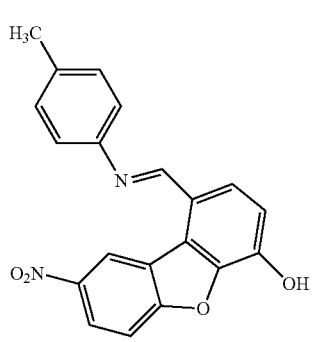
(E¹)

with CHClF₂ to yield 1-{[(4-methylphenyl)imino]methyl}-8-nitro-dibenzo[b,d]furan-4-ol (E²).

21. The method of claim 20, which further comprises converting 1-{[(4-methylphenyl)imino]methyl}-4-difluoromethoxy-8-nitro-dibenzo[b,d]furan (E²) to N-(3,5-dichloropyrid-4-yl)-4-difluoromethoxy-8-methanesulfonamido-dibenzo[b,d]furan-1-carboxamide or a pharmaceutically acceptable salt thereof.

22. A method for the preparation of p-nitrophenyl-4-difluoromethoxy-8-nitro dibenzo[b,d]furan-1-carboxylic acid ester (H) which comprises the step of reacting 4-difluoromethoxy-8-nitro-dibenzofuran carboxylic acid (G) with para-nitro phenol (G¹)

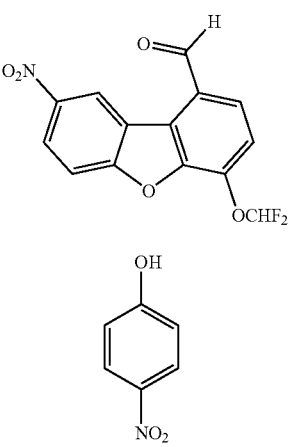

to yield p-nitrophenyl 4-difluoromethoxy-8-nitro dibenzofuran carboxylic acid ester (H).

23. The method of claim 22, which further comprises converting p-nitrophenyl-4-difluoromethoxy-8-nitro dibenzo[b,d]furan-1-carboxylic acid ester (H) to N-(3,5-dichloropyrid-4-yl)-4-difluoromethoxy-8-methanesulfonamido-dibenzo[b,d]furan-1-carboxamide or a pharmaceutically acceptable salt thereof.

24. A method for the preparation of N-(3,5-dichloropyrid-4-yl)-4-difluoromethoxy-8-nitrodibenzo[b,d]furan-1-carboxamide (I) which comprises the step of reacting p-nitrophenyl-4-difluoromethoxy-8-nitro dibenzo[b,d]furan-1-carboxylic acid ester (H) with 4-amino-3,5-dichloropyridyl (H¹)

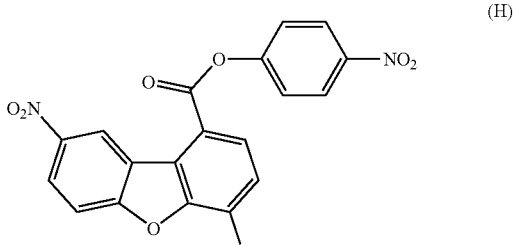
(H)

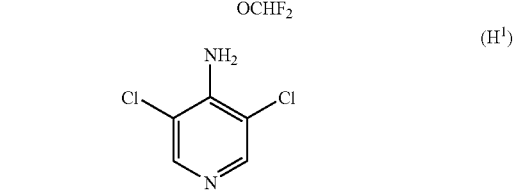
(H¹)

to yield N-(3,5-dichloropyrid-4-yl)-4-difluoromethoxy-8-aminodibenzo[b,d]furan-1-carboxamide (I).

25. The method of claim 24, which further comprises converting N-(3,5-dichloropyrid-4-yl)-4-difluoromethoxy-8-nitrodibenzo[b,d]furan-1-carboxamide to N-(3,5-dichloropyrid-4-yl)-4-difluoromethoxy-8-methanesulfonamido-dibenzo[b,d]furan-1-carboxamide or a pharmaceutically acceptable salt thereof.

26. A compound of the formula

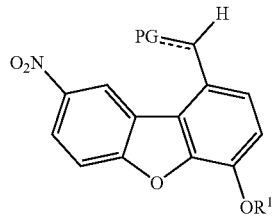

(E-I)

or a salt thereof, where
   $R^1$ is hydrogen or a substituted or unsubstituted $C_{1-6}$ alkyl, and
   PG is an aldehyde protecting group.

27. A compound of the formula

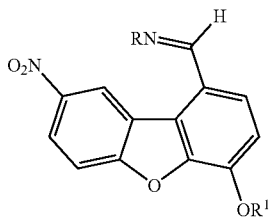

or a salt thereof, where
   R is a substituted or unsubstituted alkyl, substituted or unsubstituted alkoxy, substituted or unsubstituted cycloalkyl, substituted or unsubstituted cycloalkylalkyl, substituted or unsubstituted aryl, substituted or unsubstituted arylalkyl, substituted or unsubstituted heteroaryl, substituted or unsubstituted heteroarylalkyl, substituted or unsubstituted heterocyclic group, substituted or unsubstituted heterocyclylalkyl, and
   $R^1$ is hydrogen or a substituted or unsubstituted $C_{1-6}$ alkyl.

28. A compound of claim 27, where R is a substituted or unsubstituted aryl.

29. A compound of claim 28, where R is 4-methylphenyl.

30. A compound of claim 27, where $R^1$ is hydrogen.

31. A compound of claim 27, where $R^1$ is $CHF_2$.

32. A method for the synthesis of N-(3,5-dichloropyrid-4-yl)-4-difluoromethoxy-8-methanesulfonamido-dibenzo[b,d]furan-1-carboxamide or a pharmaceutically acceptable salt thereof which comprises the step of converting a compound having the formula:

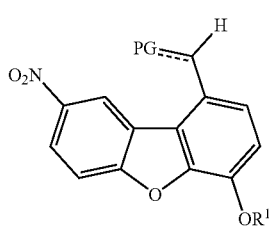

(E-I)

where
   $R^1$ is hydrogen or a substituted or unsubstituted $C_{1-6}$ alkyl, and
   PG is an aldehyde protecting group;
to N-(3,5-dichloropyrid-4-yl)-4-difluoromethoxy-8-methanesulfonamido-dibenzo[b,d]furan-1-carboxamide or a pharmaceutically acceptable salt thereof.

33. A compound selected from:
4-cyclopentyloxy-3-(4'-nitro-2'-bromophenoxy)benzaldehyde (C);
1-{[(4-methylphenyl)imino]methyl}-8-nitro-dibenzo[b,d]furan-4-ol ($E^1$);
1-{[(4-methylphenyl)imino]methyl}-4-difluoromethoxy-8-nitro-dibenzo[b,d]furan ($E^2$); and
p-nitrophenyl-4-difluoromethoxy-8-nitro dibenzo[b,d]furan-1-carboxylic acid ester (H).

* * * * *

UNITED STATES PATENT AND TRADEMARK OFFICE
CERTIFICATE OF CORRECTION

PATENT NO. : 7,563,900 B2
APPLICATION NO. : 11/251567
DATED : July 21, 2009
INVENTOR(S) : Gopalan Balasubramanian et al.

It is certified that error appears in the above-identified patent and that said Letters Patent is hereby corrected as shown below:

On the title page, item (54) and col. 1, line 1, in the title, please delete "PROCESS FOR THE PREPARATION N-(3,5-DICHLOROPYRID-4-YL)-4-DIFLUOROMETHOXY-8-METHANESULFONAMIDO-DIBENZO[B,D]FURAN-1-CARBOXAMIDE" and insert -- PROCESS FOR THE PREPARATION OF N-(3,5-DICHLOROPYRID-4-YL)-4-DIFLUOROMETHOXY-8-METHANESULFONAMIDO-DIBENZO[B,D]FURAN-1-CARBOXAMIDE -- therefor.

Signed and Sealed this
Twenty-eighth Day of February, 2012

David J. Kappos
*Director of the United States Patent and Trademark Office*